US011337360B2

(12) United States Patent
Anderson

(10) Patent No.: US 11,337,360 B2
(45) Date of Patent: May 24, 2022

(54) METHODS AND SYSTEMS FOR REDUCING SOIL COMPACTION USING WORKSITE TREATMENT BASED ON DETERMINED SOIL PROPERTIES

(71) Applicant: DEERE & COMPANY, Moline, IL (US)

(72) Inventor: Noel W. Anderson, Fargo, ND (US)

(73) Assignee: Deere & Company, Moline, IL (US)

( * ) Notice: Subject to any disclaimer, the term of this patent is extended or adjusted under 35 U.S.C. 154(b) by 139 days.

(21) Appl. No.: 16/662,407

(22) Filed: Oct. 24, 2019

(65) Prior Publication Data

US 2021/0120730 A1    Apr. 29, 2021

(51) Int. Cl.
*A01B 79/00* (2006.01)
*A01B 79/02* (2006.01)
*G01N 33/24* (2006.01)
*G05D 1/02* (2020.01)

(52) U.S. Cl.
CPC ............ *A01B 79/005* (2013.01); *A01B 79/02* (2013.01); *G01N 33/246* (2013.01); *G05D 1/0212* (2013.01); *G01N 2033/245* (2013.01); *G05D 2201/0201* (2013.01)

(58) Field of Classification Search
CPC .... A01B 79/005; A01B 79/02; G01N 33/246; G01N 2033/245; G05D 1/0212
USPC .......................................................... 701/50
See application file for complete search history.

(56) References Cited

U.S. PATENT DOCUMENTS

| 8,195,342 B2* | 6/2012 | Anderson ............ G05D 1/0088 701/1 |
| 9,066,465 B2 | 6/2015 | Hendrickson et al. |
| 9,511,633 B2 | 12/2016 | Anderson et al. |
| 10,165,725 B2 | 1/2019 | Sugumaran et al. |
| 2008/0063473 A1* | 3/2008 | Congdon ............... E01C 19/288 404/75 |
| 2008/0140431 A1 | 6/2008 | Anderson et al. |
| 2013/0046418 A1* | 2/2013 | Anderson ............... G07C 5/085 701/2 |
| 2013/0046439 A1* | 2/2013 | Anderson ............. B60C 23/002 701/36 |

(Continued)

FOREIGN PATENT DOCUMENTS

| EP | 2508057 A1 | 10/2012 |
| WO | WO2013025890 A1 | 2/2013 |

OTHER PUBLICATIONS

J. Wang, A simple method for the estimation of thermal inertia, Geophysical Research Letters, dated Mar. 6, 2010, pp. 5, vol. 37.

(Continued)

*Primary Examiner* — Yazan A Soofi

(57) ABSTRACT

Systems, methods, and devices for receiving soil parameter data of a worksite and identifying one or more locations of the worksite for treatment based on the received soil parameter data are disclosed. In some implementations, the soil parameter data include thermal latency data. Soil compaction data of the worksite may be derived from the thermal latency data. A soil parameter map of the worksite may be generated based on the received soil parameter data, and a plan of action, such as identifying one or more locations to perform a soil treatment operation, may be determined based on the soil parameter map.

20 Claims, 8 Drawing Sheets

(56) References Cited

U.S. PATENT DOCUMENTS

| | | | | |
|---|---|---|---|---|
| 2014/0257911 | A1* | 9/2014 | Anderson | G06Q 10/06315 705/7.25 |
| 2016/0018224 | A1* | 1/2016 | Isler | G05D 1/0274 701/25 |
| 2018/0044888 | A1* | 2/2018 | Chi | G06F 3/0484 |
| 2018/0092295 | A1* | 4/2018 | Sugumaran | A01C 23/007 |
| 2018/0179719 | A1* | 6/2018 | Wisley | E02F 9/261 |
| 2018/0257657 | A1* | 9/2018 | Blank | B60W 50/14 |
| 2018/0267008 | A1* | 9/2018 | Sutton | G06T 7/70 |
| 2019/0050948 | A1* | 2/2019 | Perry | G06Q 10/04 |
| 2019/0050949 | A1* | 2/2019 | Orsini | G06Q 50/06 |
| 2019/0113936 | A1* | 4/2019 | Anderson | B64C 39/024 |
| 2019/0114847 | A1* | 4/2019 | Wagner | G05D 1/0016 |
| 2019/0147094 | A1* | 5/2019 | Zhan | G06F 17/10 707/718 |
| 2019/0387658 | A1* | 12/2019 | Henry | A01B 76/00 |
| 2021/0094535 | A1* | 4/2021 | Thompson | G01C 21/005 |

OTHER PUBLICATIONS

Eleanor E Campbell, Current developments in soil organic matter modeling and the expansion of model applications, Environmental Research Letters, retrieved from internet <https://iopscience.iop.org/article/10.1088/1748-9326/10/12/123004> dated Oct. 16, 2019, pp. 37.

Dianjun Zhang, Estimation of Soil Moisture from Optical and Thermal Remote Sensing, dated Aug. 17, 2016, pp. 29.

Jacqueline R. England, Proximal sensing for soil carbon accounting, dated May 15, 2018, pp. 22.

Dai Matsushima, Soil Moisture Estimation Using Thermal Inertia Potential and Sensitivity to Data Conditions, Journal of Hydrometeorology, dated Oct. 12, 2011, pp. 11, vol. 13.

Chenyang Cui, Soil Moisture Mapping from Satellites: An Intercomparison of SMAP, SMOS, FY3B, AMSR2 and ESA CCI over Two Dense Network Regions at Different Spatial Scales, dated Dec. 25, 2017, pp. 19.

Omar T. Farouki, Thermal Properties of Soils CRREL Monograph 81-1, dated Dec. 1981, pp. 155.

Huang Qiu, Thermal Remote Sensing of Soil Moisture: Validation of Presumed Linear Relation between Surface Temperature Gradient and Soil Moisture Content, dated Nov. 2006, pp. 51.

R.W.SHEARD, Understanding Turf Management—Soil structure, density and porosity, Dec. 1991, pp. 2.

Larry Pitts, Monitoring Soil Moisture for Optimal Crop Growth, dated Mar. 12, 2016, pp. 25.

M. R. Carter, Relative Measures of Soil Bulk Density to Characterize Compaction in Tillage Studies of Fine Sandy Loams, Aug. 1991, pp. 16.

Imagery Comes of Age; Remote Imagery is Soaring to New Heights as a Crop Production Tool, Jul. 27, 2017, pp. 9.

Soil Bulk Density / Moisture / Aeration, May 2019, pp. 11.

European Search Report issued in counterpart application No. 20198028.1 dated Feb. 23, 2021 (10 pages).

* cited by examiner

METHODS AND SYSTEMS FOR REDUCING SOIL COMPACTION USING WORKSITE TREATMENT BASED ON DETERMINED SOIL PROPERTIES

FIELD OF THE DISCLOSURE

The present disclosure relates generally to determining soil properties.

BACKGROUND OF THE DISCLOSURE

Generally, soil is formed of solid material, water, and air. When soil is saturated, air is displaced by water so that the soil contains only solid matter and water. Water has different physical properties than the solid matter, and the ratio between the water and the solid matter can be determined.

SUMMARY OF THE DISCLOSURE

According to an aspect, the present disclosure is directed to a computer-implemented method performed by one or more processors for selectively determining one or more areas of a worksite for treatment. The method may include receiving soil parameter data of a worksite; generating a soil parameter map based on the received soil parameter data; generating a plan of action based on the soil parameter map, the plan of action defining an operation of an agricultural machine according to the soil parameter map; and controlling the operation of the agricultural machine according to the plan of action.

Another aspect of the present disclosure is directed to a computer program product encoded on a non-transitory medium. The computer product including computer readable instructions for causing one or more processors to perform operations including: receiving soil parameter data of a worksite; generating a soil parameter map based on the received soil parameter data; generating a plan of action based on the soil parameter map, the plan of action defining an operation of an agricultural machine according to the soil parameter map; and controlling the operation of an agricultural machine according to the plan of action.

Another aspect of the present disclosure is directed to an agricultural machine for selectively determining one or more areas of a worksite for treatment. The agricultural machine may include one or more processors and a non-transitory computer-readable storage medium coupled to the one or more processors and storing programming instructions for execution by the one or more processors, the programming instructions instruct the one or more processors to: receive soil parameter data of a worksite; generate a soil parameter map based on the received soil parameter data; generate a plan of action based on the soil parameter map, the plan of action defining an operation of an agricultural machine according to the soil parameter map; and control the operation of the agricultural machine according to the plan of action.

The various aspects may include one or more of the following features. Image data of the worksite may be received, and the soil parameter data of the worksite may be extracted from the received image data. The image data of the worksite may include thermal latency data, and extracting the soil parameter data of the worksite from the received image data may include extracting soil compaction data of the worksite. A soil measuring event may be detected, and the image data of the worksite may be received upon detecting the soil measuring event. Detecting a soil measuring event may include detecting one of a fully saturated soil moisture level or a fully dry soil moisture level. The soil parameter data may include soil compaction data. Generating a soil parameter map based on the determined soil parameter data may include generating a soil compaction map. Generating a plan of action based on the soil parameter map may include determining one or more locations of the worksite having soil compaction at or above a selected level. Controlling the operation of the agricultural machine according to the plan of action may include operating the agricultural machine to selectively till the one or more locations of the worksite having soil compaction at or above the selected level. A course through the worksite may be generated based on the soil parameter map, and at least one of direction and speed of the agricultural machine may be controlled to cause the agricultural machine to follow the generated course.

The various aspects of the present disclosure may also include one or more of the following features. The computer program product may include computer readable instructions for causing one or more processors to perform operations including: receiving soil parameter data of a worksite; generating a soil parameter map based on the received soil parameter data; generating a plan of action based on the soil parameter map, the plan of action defining an operation of an agricultural machine according to the soil parameter map; and controlling the operation of an agricultural machine according to the plan of action. Computer readable instructions for causing one or more processors to perform operations may also include receiving image data of the worksite and extracting the soil parameter data of the worksite from the received image data. Computer readable instructions for causing the one or more processors to perform operations may include detecting a soil measuring event and receiving the image data of the worksite upon detecting the soil measuring event. Computer readable instructions for causing the one or more processors to perform operations including: generating a course through the worksite based on the soil parameter map; and controlling at least one of direction and speed of the agricultural machine to cause the agricultural machine to follow the generated course.

The various aspects of the present disclosure may also include one or more of the following features. Programming instructions may include programming instructions operable to instruct the one or more processors to: receive image data of the worksite; and extract the soil parameter data of the worksite data from the received image data. The programming instructions operable to instruct the one or more processors to extract the soil parameter data of the worksite from the received image data may include programming instructions operable to instruct the one or more processors to extract soil compaction data of the worksite. Programming instructions may include programming instructions to instruct the one or more processors to: detect a soil measuring event and receive the image data of the worksite upon detecting the soil measuring event. The programming instructions operable to instruct the one or more processors to detect a soil measuring event may include programming instructions operable to instruct the one or more processors to detect one of a fully saturated soil moisture level or a fully dry soil moisture level. The programming instructions operable to instruct the one or more processors to generate a soil parameter map based on the determined soil parameter data may include programming instructions operable to instruct the one or more processors to generate a soil compaction map. The programming instructions operable to instruct the one or more processors generating a plan of action based on the soil parameter map may include programming instructions operable to instruct the one or more processors to determine one or more locations of the worksite having soil compaction at or above a selected level. The programming instructions operable to instruct the one or more processors to control the operation of the agricultural machine according to the plan of action may include programming instructions operable to instruct the one or more processors to operate the agricultural machine to selectively till the one or more locations of the worksite having soil compaction at or above the selected level.

Other features and aspects will become apparent by consideration of the detailed description and accompanying drawings.

BRIEF DESCRIPTION OF THE DRAWINGS

The detailed description of the drawings refers to the accompanying figures in which.

DETAILED DESCRIPTION

Figure 1:
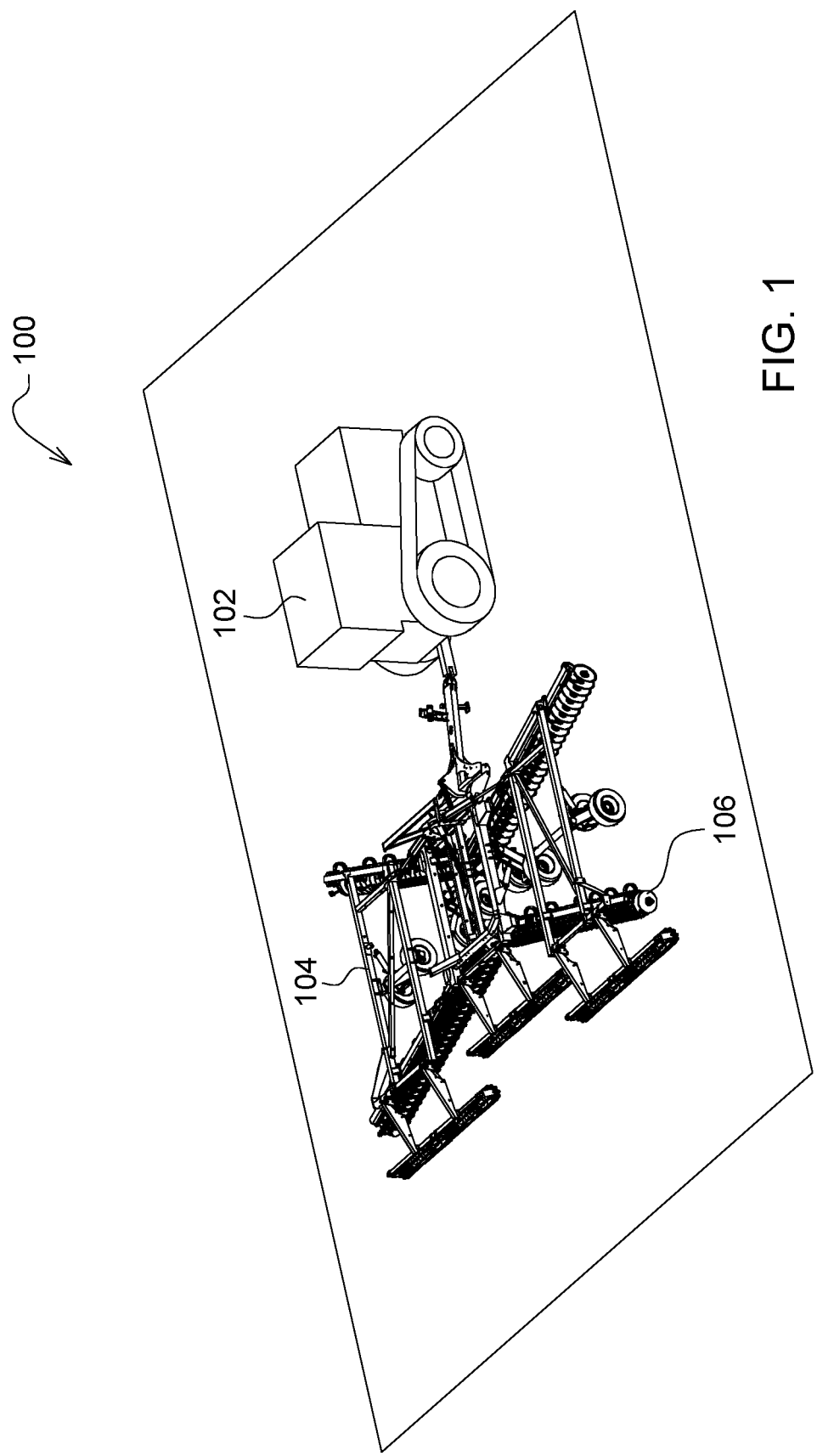
FIG. 1 is a perspective view of an example agricultural system, according to some implementations of the present disclosure.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. It is fully contemplated that the features, components, and/or steps described with respect to one implementation may be combined with the features, components, and/or steps described with respect to other implementations of the present disclosure.

The present disclosure is directed systems and methods for reducing soil compaction using soil properties, such as at a field or other area (collectively and interchangeably referred to as "worksite"). For example, thermal latency of soil of a worksite may be used to determine soil porosity. The determined soil porosity may be further refined using other types of information, such soil organic matter content of the soil and thermal trend of the soil. The determined soil porosity is used to determine soil parameters, such as bulk soil density, soil compaction, soil drainage capability, and soil root restriction. This determined information may then be used to take steps in reducing soil compaction. For example, the determined information may be used to generate a soil density map or a soil compaction map; plan a transportation route through a worksite to control compaction; determine yield analytics (e.g., determine yield estimates over a worksite based on associated soil compaction); determine a map that estimates crop root restriction within the soil based on associated soil compaction; or determine a ground truth comparison map. Other types of information may also be produced using the determined information.

FIG. 1 is a perspective view of an example agricultural system 100. In the illustrated example, the agricultural system 100 includes a tractor 102 and a tillage machine 104. The tractor 102 pulls the tillage machine 104 over a worksite to perform a tillage operation. Thus, the tractor 102 propels the tillage machine 104 over the surface of the ground so that the tillage machine 104 can perform a tillage function. Although the tractor 102 and the tillage machine 104 of the agricultural system 100 is shown as being separate components, in other implementations, the agricultural system 100 may be an integrated tillage machine, for example.

In the illustrated example, tillage machine 104 includes a plurality of tillers 106 laterally arranged. The tillers 106 may be in the form of plows, harrows, cultivators, or other devices operable to till soil. The tillage machine 104 may include one or more metering devices operable to control a depth of penetration of the soil by the tillers 106.

Although examples provided in the present disclosure are described in the context of tillage, the scope of the disclosure is not so limited. Rather, the concepts described in the present disclosure may be applicable to other soil treatment apparatuses and operations and the present disclosure is intended to encompass these other applications.

Figure 2:
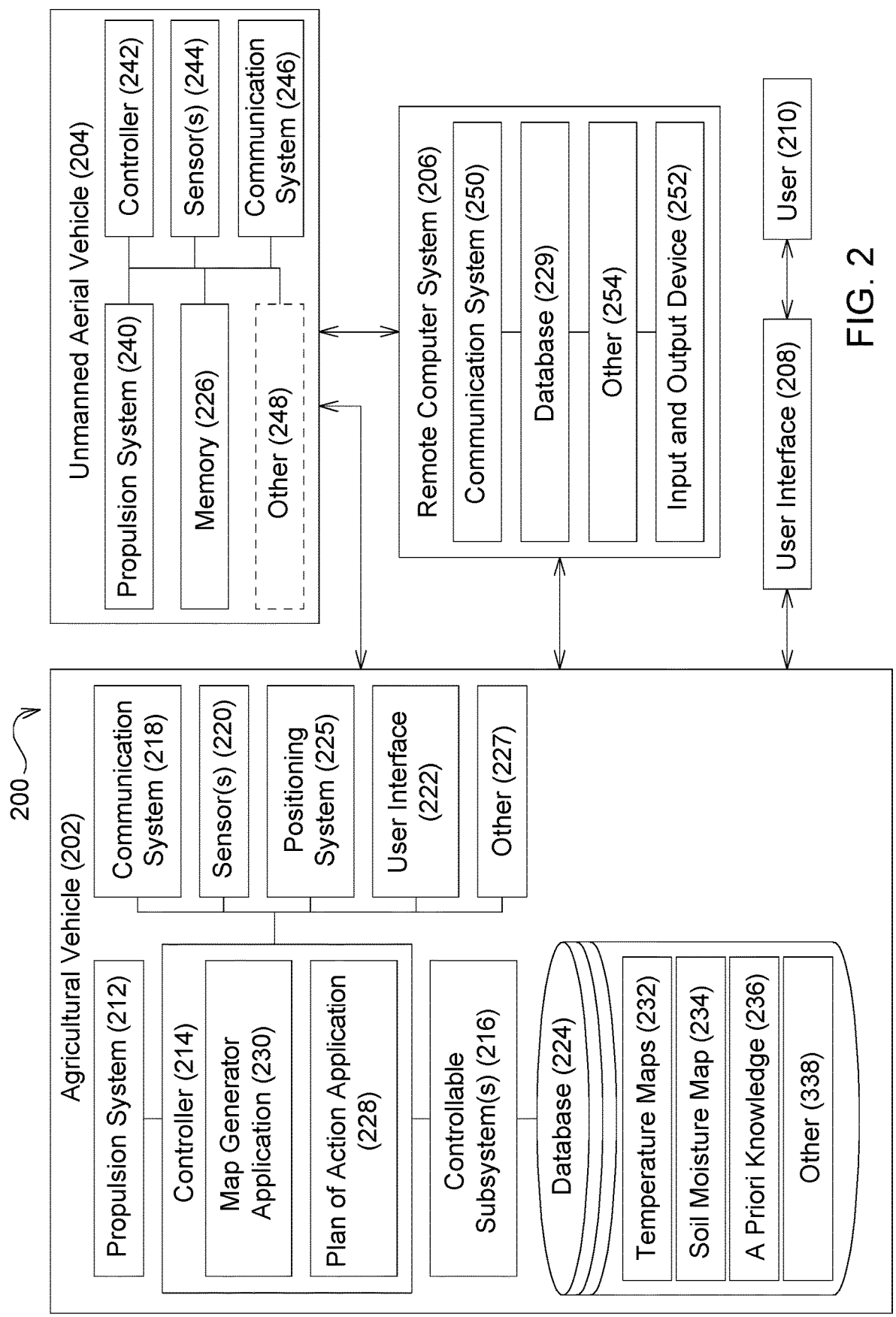
FIG. 2 is a block diagram of an example agricultural system, according to some implementations of the present disclosure.

FIG. 2 is a block diagram of an example agricultural system 200. The agricultural system 200 includes an agricultural vehicle 202, an unmanned aerial vehicle (UAV) 204, and a remote computer system 206. The remote computer system 206 may be a type of electronic computer operable to execute programs and store information electronically, as described in more detail below. The agricultural vehicle 200 includes a user interface 208. A user 210, such as an operator of the agricultural vehicle 200, engages with the user interface 208 to provide one or more inputs to, receive one or more outputs from, or otherwise control a function of the agricultural system 200, such as one or more functions of the agricultural vehicle 202, the UAV 204, the remote computer system 206, or a combination thereof.

Each of the agricultural vehicle 202, the UAV 204, and the remote computer system 206 are shown as including various features. However, while FIG. 2 illustrates one example of how these features are distributed amongst the agricultural vehicle 202, the UAV 204, and the remote computer system 206, the example of FIG. 2 is provided merely as an example. In other implementations, the various features may be distributed differently amongst the agricultural vehicle 202, the UAV 204, and the remote computer system 206. Still further, in other implementations, the agricultural system 200 may include additional features, fewer features, or different features than those illustrated and described. Consequently, agricultural systems having other arrangements of features are contemplated within the scope of the present disclosure. Further, although a single remote computer system 206 is present in the illustrated example, in other implementations, a plurality of remote computer systems 206 may be used. Further, the remote computer system 206 may be in the form of one or more servers. Still further, in other implementations, the agricultural system 200 may have additional components, such as one or more additional agricultural vehicles, one or more additional UAVs, or other components.

In some implementations, the agricultural vehicle 202 may be a tillage system operable to till soil. For example, the agricultural vehicle 202 may be the agricultural system 100 described above with respect to FIG. 1. In the illustrated example of FIG. 2, the agricultural vehicle 202 includes a propulsion system 212, a controller 214, one or more controllable subsystems 216, a communication system 218, one or more sensors 220, a user interface 222, a database 224, and a positioning system 225. In some implementations, the agricultural vehicle 202 may include one or more other components 227.

The controller 214 is operable to control operation of one or more aspects of the agricultural vehicle 202, including operation of controllable subsystems 216. The controller 214 may be in the form of an electronic computer having one or more processors configured to execute applications and one or more memory devices configured to store data and programs electronically. The controllable subsystems 216 include, for example, one or more depth adjustment systems, a system to control a direction of the agricultural vehicle 202 (e.g., a steering system), or other system. For example, in some implementations, the controller 214 is operable to generate a control signal to adjust depth at which one or more tillers extend into the soil or a load applied to the one or more tillers during operation of the agricultural vehicle 202. For example, in some implementations, the extent to which the controller 214 extends the one or more tillers into the soil or a load applied to the one or more tillers may vary in response to one or more detected soil parameters, such as a soil compaction level or soil moisture level. Further, the controller 214 is operable to control the propulsion system 212. Thus, in some implementations, the controller 214 is operable to control a speed and direction of the agricultural vehicle 202 along with, for example, operation of a farming implement, such as a tillage device.

The database 224 may be in the form of one or more electronic memory devices and is configured to store information electronically such as temperature map data 232, soil moisture map data 234, a priori knowledge 236, as well as other data 238. The controller 214 is operable to send information to or receive information from the database 224. However, while database 224 is illustratively shown in FIG. 2 as part of agricultural vehicle 202, information described as being contained in the database 224 may also be stored on the remote computer system 206 (such as within database 229, within a memory 226 of the UAV 204, or in another location accessible through a network, for example). The database 229, the memory 226, or both may be one or more electronic memory devices that is configured to store data electronically. The network may be, for example, a cloud-based network or another networked infrastructure. In some implementations, the information utilized by the agricultural system 200 may be distributed among the different storage locations.

The controller 214 may include logic for executing a plan of action application 228 and a map generator application 230. The plan of action application 228 and the map generator application 230 may be applications that include software instructions operable to cause the controller 214 to operate in a manner as defined by the software instructions. The map generator application 230 is operable to generate a map, as described in greater detail below. The controller 214 is coupled to the one or more sensors 220. The sensors 220 are operable to sense a wide variety of different properties. For instance, in some implementations, the sensors 220 may include one or more temperature sensors, soil moisture sensors, as well as sensors related to the controllable subsystems 216. In some implementations, the sensors 220 may include a load sensor or a depth sensor, such as a depth sensor for a tiller.

The positioning system 225 provides an indication of a geographic location of the agricultural vehicle 202 relative to a location on the earth, an orientation of the agricultural vehicle 202 relative to a location on the earth, or both. For example, in some implementations, the positioning system 225 is a Global Positioning System (GPS). The communication system 218 is configured to communicate with the UAV 204 and the remote computer system 206. Communication may take place over a wired or wireless link using any of a variety of different techniques. In other implementations, the communication system 225 may be or form a part of a mobile device. For example, the communication system 225 may form part of a smartphone, a tablet computer, a laptop computer, or other portable computer. The user 210 may interact with the communication system 225 to facilitate communication between two or more of the agricultural vehicle 202, the UAV 204, and the remote computer system 206.

The user interface 222 is used by the user 210 to control various aspects of the agricultural vehicle 202, such as actuation of the controllable subsystems 216, the propulsion system 212, or some other aspect of the agricultural vehicle 202. The user interface may include one or more levers, pedals, a steering wheel, joystick, buttons, touch screen, or other input devices. In some implementations, the user interface 222 may also include a display device, audio, device, a haptic device, an electric or electronic input devices, or a wide variety of other devices for providing inputs to the agricultural vehicle 202 or for receiving output from the agricultural vehicle 202.

In the illustrated example, the UAV 204 includes a propulsion system 240, a controller 242, the memory 226, one or more sensors 244, a communication system 246, and, in some implementations, other features 248. The controller 242 may be in the form of one or more electronic processors, and the memory 226 may be in the form of one or more electronic memory devices. The controller 242 is operable to control operation of one or more aspects of the UAV 204. For example, in some implementations, the controller 242 is operable to control the propulsion system 246. Thus, in some implementations, the controller 242 is operable to control a speed, course, and altitude of the UAV 204. The controller 242 is also operable to receive information from the one or more sensors 244 and, in some instances, send information to the one or more sensors 244. In some implementations, the sensors 244 include a geo-positioning sensor that senses a position of UAV 204 and one or more cameras operable to take images using light within a visual range, an infrared range, or another range of wavelengths. For example, in some implementations, the UAV 202 is operable obtain an infrared image of an area of the earth's surface, such as a field or other worksite, in order to determine soil temperatures. The determined soil temperatures information may be used, for example, to determine thermal latency, which may then be used to derive soil properties, such as a moisture content of the soil.

Data captured from sensors 244 may be stored within the memory 226 of the UAV 202. In some implementations, the information from the sensors 244 may be transmitted to the agricultural vehicle 202 via the communication systems 246 and 218. Additionally, the information from sensors 244 may be transmitted to the remote computer system 206 where the information may be stored in the database 229.

In some implementations, the remote computer system 206 may be a remote service (e.g., a cloud-based service or other service that is remotely accessible) or a server provided at a remote location. In the illustrated example, the remote computer system 206 includes a communication system 250, the database 229 (which may be in the form of one or more memory devices), and a user interface 252. In other implementations, the remote computer system 206 may include other features 254.

The communication system 250 is operable to communicate with the agricultural vehicle 202 and the UAV 204. For example, the communication system 250 of the remote computer system 206 may communicate with the communication systems 218 and 246 of the agricultural vehicle 202 and the UAV 204, respectively. While FIG. 2 illustrates different functionality ascribed to each of agricultural vehicle 202, the UAV 204, and remote computer system 206, it is to be understood that, in at least some examples, the functionality is differently apportioned among the agricultural vehicle 202, the UAV 204, and the remote computer system 206.

According to an example operation of some implementations, the UAV 204 obtains at least one georeferenced image of a surface of the earth, such as a field or portion of a field, using the sensors 244. As explained above, the sensors 244 may include one or more cameras operable to obtain images using different frequencies of light. An image obtained by the sensors 244 is transmitted to the agricultural vehicle 202 where it is processed, for example by the controller 216, along with a priori knowledge 236, to generate a site-specific plan of action application 228. In other implementations, the image data obtained by the sensors 244 may be processed on the UAV 204, by the remote computer system 206, by the agricultural vehicle 202, or a combination of these. A priori knowledge 236 includes, for example, knowledge particular to known soil conditions, soil type, drainage conditions (such as drainage tile and conduit layouts), etc. The plan of action application 228 may, for example, determine a plan of action to be performed, at least in part, by the agricultural vehicle 202. For example, the plan of action may define a depth level for a tillage machine that indicates a prescribed depth of tillage to reduce or eliminate soil compaction at one or more locations of a worksite.

The map generator application 230 present in the controller 214 is operable to generate a soil parameter map using, for example, the image data obtained by the sensors 244. The map generator application 230 may use the image data as an input, process image data as an input, or both. For example, the map generator application 230 may utilize soil parameter data derived from the image data. The plan of action application 228 may utilize the soil parameter map, for example, to identify one or more locations of a worksite for which tillage is desired. Thus, the generated soil parameter map and the generated plan of action may be used, for example, to determine where tillage is desired and how a tillage depth should change at different locations in the field in order to reduce soil compaction. The controller 214 generates a signal to control the controllable subsystems 216, such as a tillage machine. The tillage machine is controlled according to the generated signal such that the tillage depth specified by the plan of action application 228 is achieved according to the generated soil parameter map. In some implementations, the agricultural vehicle 202 includes a closed loop control system such that an actual depth measured by a tillage machine depth sensor (included in the sensors 220, for example) is then reported back to controller 214. The controller 214 provides signals to the tillage machine to adjust a depth of one or more tillers based on the measured depth and the prescribed depth.

While the example described immediately above is in the context of control of a tillage machine, other examples in which systems and methods described herein may be used are also within the scope of the present disclosure. Some examples include seed bed preparation, harvest site preparation, construction site preparation, turf site preparation, as well as forestry site preparation. Further, although a UAV 204 is described, other types of equipment may be used to obtain data of a worksite, such as image data. For example, one or more satellites orbiting the earth may be used alone or in combination with the UAV 204 to provide information to the agricultural vehicle 202, the remote computer system 206, or both.

Figure 3:
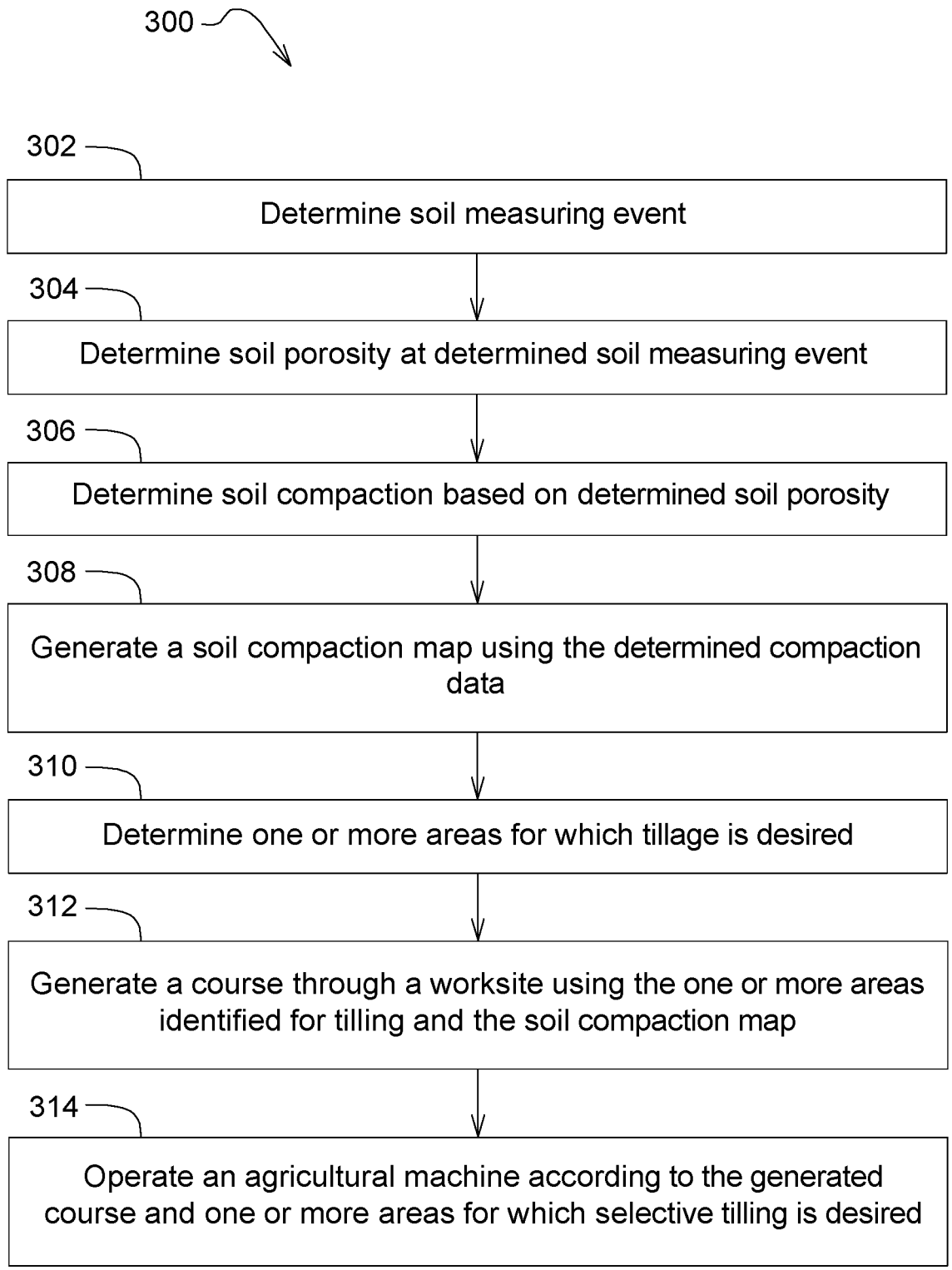
FIG. 3 is a flowchart of an example method of determining soil properties and using the determined properties, according to some implementations of the present disclosure.

FIG. 3 is a flowchart of an example method 300 of determining soil properties and using the determined soil properties. The example method of FIG. 3 involves determining soil porosity and utilizing the determined soil porosity to determine soil compaction. The determined soil compaction is utilized to determine, for example, where tillage may be used in order to reduce or alleviate soil compaction. At 302, a soil measuring event is determined. Particularly, at 302, a determination is made as to when a moisture content of soil of a worksite is measured.

In some implementations, determining a soil measuring event is premised on water content of the soil. For example, in some implementations, a soil measuring event exists when a moisture content of the soil obtains a target level. In some implementations, the target moisture content level is a fully saturated level. In other implementations, the target moisture content level is a fully dry level, i.e., when the soil lacks moisture. Generally, soil is a combination of solid material (i.e., mineral content), water, and air. Each of these components has an associated heat capacity or mass specific heat (e.g., calories/gram ° C.) and a density (e.g., grams/cubic centimeter). A composite heat capacity, C, for a volume of soil is a weighted sum of the products of mass specific heat multiplied by the density for each soil component. A volume fraction for each component is included in order to provide a weighting for each component. A mathematical representation of this concept is provided as follows:

$$C_{soil} = [(f_{mineral} \times c_{mineral} \times \rho_{mineral}) + (f_{water} \times c_{water} \times \rho_{water}) + (f_{air} \times c_{air} \times \rho_{air})],$$ Equation 1 where $C_{soil}$ is the heat capacity of a soil; $f_{mineral}$ is the volume fraction of mineral in the soil; $c_{mineral}$ is the mass specific heat of the soil mineral(s); $\rho_{mineral}$ is the density of the soil mineral(s); $f_{water}$ is the volume fraction of water in the soil; $c_{water1}$ is the mass specific heat of the water in the soil; $\rho_{water}$ is the density of water; $f_{air}$ is the volume fraction of air in the soil; $c_{air}$ is the mass specific heat of the air; and $\rho_{air}$ is the density of the air. The volume fractions of the different soil components add to one, as shown in Equation 2 below:

$$f_{mineral} + f_{water} + f_{air} = 1 \qquad \text{Equation 2}$$

Thermal inertia relates to the rate at which a surface temperature of soil changes in response to energy flow. Changes in energy flow may result from, for example, changes in sunlight, ambient air temperature, or both. Thermal inertia is proportional to the square root of soil mass specific heat times the soil density times the soil thermal conductivity. A mathematical relationship of this concept is provided as follows:

$$I_{soil} \propto \sqrt{c_{soil} \times \rho_{soil} \times k_{soil}}, \qquad \text{Equation 3}$$

where $I_{soil}$ is the thermal inertia of the soil; $c_{soil}$ is the composite mass specific heat of the soil; $\rho_{soil}$ is the density of the soil; and $k_{soil}$ is the thermal conductivity of the soil. Thermal latency, also called thermal lag, refers to a time delay between a change in sunlight or atmospheric temperature presented to a soil surface and a resulting change in soil surface temperature. Thermal latency is proportional to thermal inertia, which is represented by the following mathematical relationship:

$$L_{soil} \propto I_{soil}, \qquad \text{Equation 4}$$

where $L_{soil}$ represents thermal latency of the soil and where $I_{soil}$ represents thermal inertial of the soil. Thus, a soil having a greater moisture content has a greater thermal inertia than the same soil with a reduced moisture content or a dry soil. Further, for the same conditions, a soil having a greater moisture content has a greater thermal latency than a dry soil or a soil with a decreased moisture content. Thus, a soil having a greater moisture content takes a larger time period to warm from a first temperature to a second temperature (for example, after sunrise) than the same soil having a decreased moisture content, such as a dry soil.

At full saturation, the air present in soil is displaced by water, such that the soil contains the solid material and water to the exclusion of the air. In such a condition, because the solid material and the water have different thermal properties, a percentage of the soil occupied by the solid material and a percentage of the soil occupied by water is determinable, such as by thermal latency measurements. These thermal latency measurements reflect the thermal inertia of the existing water and solid (i.e., mineral) content of the soil. The portion of the soil occupied by water represents porous space within the saturated soil. Determining the amount of space within the soil may be used to determine the porosity of the soil and, consequently, a level of compaction of the soil. Alternatively, the soil measuring event may be a fully dry condition. At a fully dry condition, the soil lacks moisture, such that the soil is a combination of solid material and air. Once again, the space within the soil is determinable using, for example, thermal latency measurements, and the porosity of the soil is determinable. Soil compaction may then be determined.

Identifying a selected soil moisture level used to determine a soil measuring event may be performed in several ways. For example, the target moisture level of the soil may be determined using rainfall estimates. Rainfall estimates may be determined using radar data, such as doppler radar data. In the context of a target moisture level being a fully saturated level, radar data may be used to determine a fully saturated soil condition, for example, where radar data indicates a selected amount of rainfall over a selected period of time. For example, a rainfall of at or above two inches of rain in a 24-hour period may be used to indicate a fully saturated moisture level within the soil. Consequently, such radar data may be used to identify a soil measuring event. In still other instances, a fully saturated soil condition may be produced. For example, a worksite, such as a field, may be irrigated until a fully saturated condition exists to create a soil measuring event.

In other implementations, terrestrial moisture sensors may be used to detect a target moisture level within the soil and, hence, a soil measuring event. In some instances, a single terrestrial moisture sensor may be used. In other implementations, a plurality of terrestrial moisture sensors may be distributed within an area of interest. When a moisture level at or above a selected level is detected within one or more of the moisture sensors, a soil measuring event may be indicated. Example terrestrial moisture sensors include Field Connect™ produced by John Deere of One John Deere Place, Moline, Ill. 61265. Other types of moisture sensors are also within the scope of the present disclosure.

In still other implementations, satellite data may be used to detect a target moisture level in the soil. For example, data from the National Aeronautical and Space Administration's (NASA) Soil Moisture Active Passive (SMAP) satellite may be used to estimate a soil moisture level at a desired location on the earth's surface.

Moisture content of soil may also be determined using a combination of in situ sensors, such as one or more terrestrial moisture sensors, along with other types of data, such as image data, topography data, standing water data, and historic moisture data. Standing water data may be obtained from image data of an area, for example. Additionally, a terrestrial moisture sensor located, for example, on a level portion of a field, may be used detect soil saturation. Topographic data (such as in the form of a topographical map showing topographical characteristics of a field) and rainfall data may be used in combination to determine soil saturation levels. Topographical characteristics of a field may be used to identify depressions in the field, which may be saturated, and hilltops, which may or may not be saturated. Rainfall data may be used to determine saturation levels of the topographical features. For example, rainfall data indicating that a particular amount of rain fall has occurred over an extended period of time, such as a period of several days (as opposed to the same amount of rainfall over a period of a few hours within a single day), may indicate that the rainfall has soaked into the hilltop soil as opposed to running off of the hilltops and, therefore, not saturating the hilltop soil.

In still other implementations, soil moisture content may be determined using soil thermal images. Soil thermal images, particularly soil thermal images taken over time that provide a thermal trend of the soil, may be used in combination with other information, such as rainfall data, to determine a peak thermal latency of the soil. This peak thermal latency of the soil may be used to indicate a fully saturated soil condition and, therefore, a soil measuring event.

Different data sets used to determine a soil measuring event may be at different resolutions. For example, data use at an earlier step may have a different resolution than data used in later steps. For example, rainfall or soil moisture data (sensed, for example, by a weather station) may be data taken at a single location and extrapolated over a larger area while derived soil parameters may be premised, at least in part, on data measured at a millimeter or centimeter resolution over an area. In some implementations, a plurality of point data may be interpolated to obtain a more granular level of data. The interpolated data and extrapolated data at various resolutions may be combined to determine the existence of a soil measuring event.

Although fully saturated soil conditions and fully dry conditions are described as indicators of soil measuring events, the scope of the disclosure is not so limited. In other implementations, soil measuring events may be taken at different soil moisture levels. Soil moisture within a soil, particularly within a given distance from the soil surface, is dynamic. For a particular instance of water saturation, for example, in the top four inches of soil, water seeps into lower, drier layers of the soil, and water is evaporating from the soil surface. Additionally, the water may not completely displace air trapped in the soil. In the time between a full saturation event being detected or estimated and when soil temperature data can be collected, the saturation level may have decreased. However, soil temperature measurements may be obtained when soil moisture levels are as close to 100% or 0% moisture saturation as possible, recognizing logistic and measurement protocol constraints.

With a soil measuring event identified, at 304, the soil porosity is determined. Soil porosity is determined by measuring the thermal latency of the soil at the soil measuring event. In some implementations, at least two soil temperature measurements separated in time are obtained during a soil measuring event. In some implementations, at least two soil temperature measurements are obtained at a time proximate the soil measuring event, recognizing applicable logistical and measurement protocol restraints. As explained above, the thermal latency of soil is related to an amount of water relative to solid material in the soil or an amount of air relative to solid material in the soil, especially at a moisture saturation condition of the soil or at a complete dryness condition of the soil, respectively. Because the thermal inertia of solid material, water, and air are different, a porosity of a soil is determined by taking into consideration the different thermal inertias of the different materials using a thermal image of an area, such as a worksite or portion of a worksite. The composite thermal inertia of the soil has a corresponding thermal latency. Particularly, where soil is fully saturated with water, the thermal latencies of each component of the soil, i.e., water and solid material, form a composite thermal latency that is correlated into porosity of the soil. A similar correlation is possible for fully dry soil.

In some implementations, thermal latencies measured as a difference in soil surface temperatures across a worksite at two different points in time are adequate for machine control, such as the control of an agricultural machine as described in more detail below. In other implementations, other analyses incorporating additional information may be desired. For example, in another example implementation, soil surface temperatures are taken at two points in time and used in conjunction with a soil thermal model. A soil thermal model may incorporate soil temperature data at various soil depths. For example, the temperature data may be obtained at depths up to four inches below a surface of the soil. In some instances, the soil temperature data may be obtained with using soil temperature sensors and interpolating the soil temperature sensor data to obtain soil temperatures at a desired depth, e.g., four inches below the surface of the soil. In some implementations, the soil data may include frost depth data. For example, the soil thermal model may include data estimating a depth at which the soil temperature is 0° C. (32° F.). A soil thermal model may be used to estimate when soil has reached a thermal equilibrium. For example, a soil thermal model may be used to determine when the soil has reached thermal equilibrium before sunrise when temperature variations a selected amount over a number of days. For example, a soil model may detect thermal equilibrium when temperature variations over a selected number of days varies one to four degrees Celsius (33.8° F. to 39.2° F.). In some implementations, the soil thermal model may also incorporate energy flow into the soil from solar radiation, warming air at the soil surface, or both. Solar energy may be determined as a function of several variable, such as date, time, sun angle, cloud cover, soil albedo, etc. The change in soil surface temperature along with the thermal capacities of the mineral and water contained in the soil may be used to calculate the soil porosity (i.e., the portion of the soil volume occupied by water at a saturated soil condition). The determined soil porosity and soil type may be used to calculate bulk soil density and a degree of agronomic compaction. In some instances, soil type alters thermal parameters used in calculations, such as specific heat. For example, clay typically has a specific heat that is greater than a specific heat of sand. Soil type may be obtained, for example, from a soil survey map, from an in situ visual analysis of the soil, or from field or laboratory analysis of a sample of the soil.

A determined soil porosity value obtained using the thermal latency values of the soil may be further enhanced to produce a more accurate porosity with the use other information. For example, an amount of organic matter contained within the soil (referred to hereinafter as "soil organic matter" or (SOM)) may be used to improve the determined soil porosity. Generally, for agricultural soils, SOM may be in the range of 0% to 20%, and, generally, SOM has a different thermal inertia that the other soil components, i.e., mineral, water, and air. For example, SOM may be 0%, 5%, 10%, 15%, 20% or any value therebetween. Frequently, the thermal properties of SOM are consolidated with thermal properties associated with the mineral component of the soil. SOM data may be obtained from, for example, laboratory soil sample test data; near infrared (NIR) sensor data, located on the ground or in an aerial vehicle; and soil models. In some implementations, SOM data may be obtained by NIR sensors. In some implementations, the NIR sensors may sense the visible-NIR range. Further, mid-infrared range frequencies may also be measured. In some implementations, the NIR sensors may be ground-based sensors that are fixed or mobile sensors or a combination of mobile and fixed sensors. Mobile-based NIR sensors may be moveable terrestrial sensors or aerial sensors or both. Still further, some NIR sensors may be satellite-based sensors.

Soil type may also be used to improve the determined soil porosity value. Soil type identifies the types of solid material (i.e., minerals) contained within a soil and particles sizes of the solid materials. With knowledge of the solid material types forming the soil, a more precise soil porosity value is determinable.

Thermal latency data may be obtained from numerous sources. For example, thermal latency data may be obtained from satellites orbiting the earth. In some implementations, the thermal latency data is obtained by a satellite by measuring infrared radiation being emitted from the soil. Infrared frequencies may be near infrared range or the medium infrared range. For example, infrared frequencies in the range of 725 nanometers (nm) to 1 millimeter (mm) may be measured and used to determine thermal latency of the soil based on surface temperature measurements. A satellite may be used to capture thermal latency data of an area on the earth's surface on a regular basis or at any desired time. For example, a time during which thermal latency data are obtained may correspond to an orbit of the satellite.

In other implementations, the thermal latency data may be obtained by a UAV, such as the UAV 204, described above. A UAV may be advantageous in that the thermal latency data may be obtained during cloudy sky conditions that may otherwise interfere with or prevent thermal latency data acquisition by a satellite. A UAV may be made to operate below cloud cover to collect the thermal latency data of an area, such as a worksite or portion of a worksite. Further, a UAV may be made to collect data on a more desirous schedule, as opposed to a satellite whose data acquisition may be constrained by the nature of the satellite's orbit.

In still other implementations, the thermal latency data may be acquired by one or more terrestrial sensors. For example, a plurality of terrestrial sensors may be positioned at various locations in or around a worksite for which thermal latency data are desired. The terrestrial sensors may be fixed in specific locations, or, in other implementations, the terrestrial sensors may be moveable and able to be relocated to a plurality of different locations.

The thermal latency data having increased spatial resolution are obtained, particularly when the data are obtained using a satellite or a UAV. Such sources provide data having a spatial resolution on a millimeter or centimeter scale. The data obtained from these sources includes thermal latency data having spatial resolution in the millimeter or centimeter range. Soil porosity data are derivable from the thermal latency data. With porosity information on such a granular scale, soil compactness remediation remedies, described in more detail below, may be selective, thereby saving time, reducing machinery wear and tear, and reducing labor and fuel costs.

At 306, an indication of soil compaction is determined based on the soil porosity. For example, Table 1 describes a degree of compaction that is associated with the determined porosity information of a particular soil type.

TABLE 1

The relationship between soil compaction, apparent soil density, and soil porosity of a loam soil.

| Degree of Compaction | Apparent Density (grams per cubic centimeter (gm/cm$^3$)) | Total Porosity (%) | Macro Porosity (%) | Micro Porosity (%) |
|---|---|---|---|---|
| Low | 1.31 | 50.5 | 21.5 | 29.0 |
| Medium | 1.49 | 43.7 | 15.8 | 27.9 |
| High | 1.64 | 38.1 | 10.9 | 27.2 |

Figure 4:
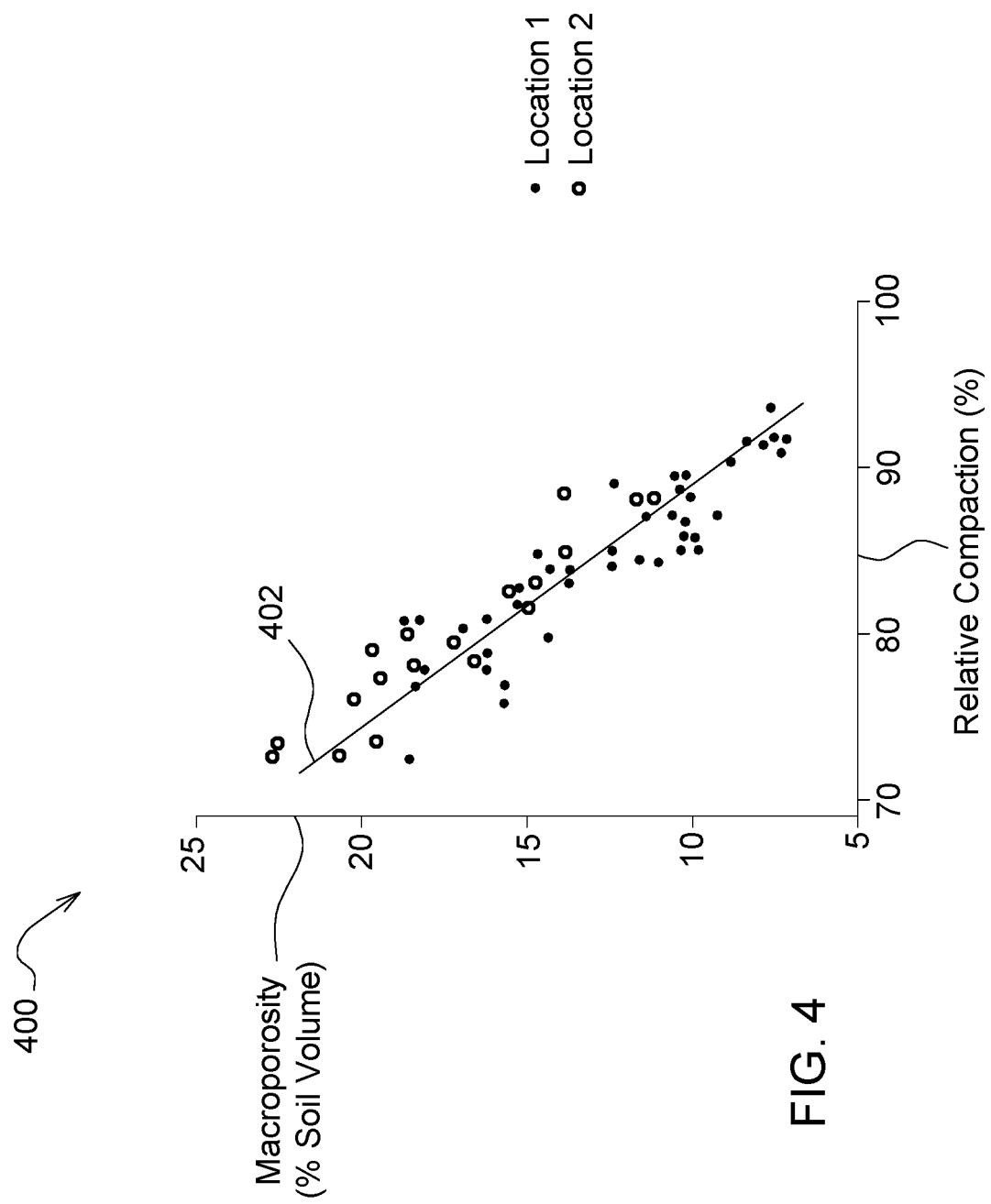
FIG. 4 is an example chart that correlates soil compaction with soil porosity for two different locations, according to some implementations of the present disclosure.

FIG. 4 is an example chart 400 that correlates soil compaction with soil porosity for two different locations. As is shown in FIG. 4, line 402 represents a linear relationship between soil porosity (in percentage (%) of soil volume) and soil compaction (in %). Consequently, soil compaction is may be obtained with the use of the determined soil porosity.

As shown with reference to Table 1, bulk density of the soil is also determinable from the soil porosity information. In some instances, bulk soil density, alone, may identify locations within a worksite for which tillage may be used to improve the compaction of the soil. In other instances, thermal latency data of a worksite obtained over time may be used to identify locations having compaction located more deeply below the surface or drainage problems present within the worksite. For example, thermal density data obtained over time may indicate areas of increased bulk density that may reflect poor drainage for which drainage remediation may implemented or damaged drainage systems that may be in need of maintenance.

Further, other types of soil parameters may also be obtained with the soil porosity information. As shown in Table 2, soil porosity may be used to obtain bulk soil density, and the bulk soil density may be used to determine areas restrictive to root growth, termed "root restriction," on a granular scale.

TABLE 2

Relationship of Soil Bulk Density to Root Growth Based on Soil Texture

| Soil Texture | Ideal Bulk Densities for Plant Growth (gm/cm$^3$) | Bulk Densities that Affect Root Growth (gm/cm$^3$) | Bulk Densities that Restrict Root Growth (gm/cm$^3$) |
|---|---|---|---|
| Sands, loamy sands | <1.60 | 1.69 | >1.80 |
| Sandy loams, loams | <1.40 | 1.63 | >1.80 |
| Sandy clay loams, clay loams | <1.40 | 1.60 | >1.75 |
| Silts, silt loams | <1.40 | 1.60 | >1.75 |
| Silt loams, silty clay loams | <1.40 | 1.55 | >1.65 |
| Sandy clays, silty clays, clay loams | <1.10 | 1.49 | >1.58 |
| Clays (>45% clay) | <1.10 | 1.39 | >1.47 |

Figure 5:
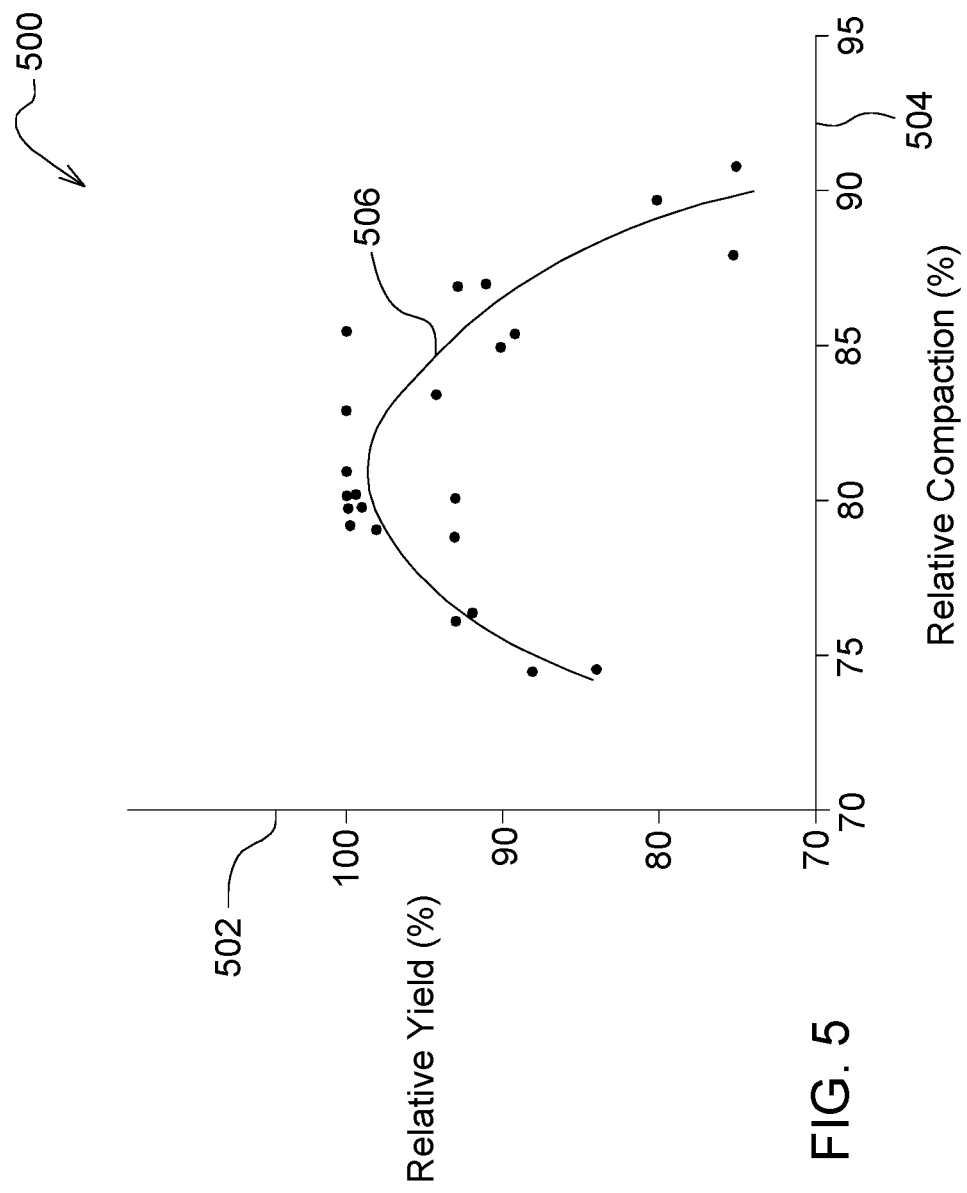
FIG. 5 is an example chart illustrating crop yield versus soil compaction, according to some implementations of the present disclosure.

Additionally, the determined soil porosity may be used to determine expected crop yield loss based on soil compaction on a granular scale. FIG. 5 is an example chart 500 illustrating relative crop yield 502 versus relative soil compaction 504. The curve 506 illustrates how soil compaction affects crop yield. The chart 500 illustrates that crop yield information is obtainable with the use of thermal latency information, such as the thermal latency information described above. Thus, relative crop yield data may also be obtained based on the determined soil porosity. Consequently, estimated crop yield on a granular level is obtainable within a worksite where thermal latency measurements have a granular spatial resolution, such as a spatial resolution in the range of one centimeter (cm) to 20 cm. In some implementations, spatial resolutions are greater than one centimeter and crop yield estimates may aggregate a plurality of plants.

Although some soil parameters are described, other soil parameters may also be obtained with the use of thermal latency. Further, like the soil parameters described above, other soil parameters may be obtained on a granular scale based on thermal latency information and other information obtainable therefrom.

Information obtained using the thermal latency, such as soil compaction, may be used to generate a variety of representational information, such as one or more maps of an area surveyed by the UAV, satellite, or other sensors operable to detect thermal latency of soil. For example, at 308 of FIG. 3, a soil compaction map of the surveyed area is generated using determined soil compaction data. As explained above, in some implementations, the obtained thermal latency data may have a spatial resolution in the millimeter or centimeter range. Consequently, the resulting soil compaction map may have the same or a similar spatial resolution of the area surveyed in terms of soil compaction. In some implementations, other types of information may be incorporated into the soil compaction map. For example, information such as soil type, topography, and soil moisture content may also be incorporated into a soil compaction map. Geopositional information may also be incorporated into the soil compaction map. The geopositional information may include longitude information, latitude information, and elevation information. Soil compaction map data is a type of georeferenced storage in which soil compaction data associated with a location is stored and available for future use.

Soil moisture information may be obtained from thermal inertial information. For example, although the soil measurement events may correspond to a soil saturation condition or a fully dry condition, thermal inertia data may be obtained at different times that may not otherwise correspond to a soil measuring event. Thermal inertia data may be obtained from sensor measurements obtained by the UAV, satellite, or terrestrial sensors. This thermal latency data correlates to soil moisture level. Thus, the thermal latency data obtained from the numerous measurements may be used to show how soil moisture changes over time. This information may be combined into a map, such as a water drainage map to identify one or more areas of a field, for example, for which drainage improvements are desired or one or more areas where existing drainage infrastructure may need repair.

At 310, the soil compaction map data are used to determine one or more locations for which tilling is desired. The one or more areas for which tillage may be desired by be generated as part of a plan of action, as described above. The one or more areas may be identified by comparing soil compaction data to a selected compaction threshold. For example, soil compaction at or above the soil compaction threshold are identified as areas for which tilling is desired. In some implementations, the selected threshold may be a soil compaction that corresponds to root restriction, crop yield loss or reduction, or another threshold.

At 312, the soil compaction information contained in the soil compaction map is used to plot a course through the surveyed worksite. Particularly, the plan of action identifying areas for which tillage is desired to reduce soil compaction is used to plot a course through a worksite. In some implementations, the plotted course defines a path through the worksite that connects areas of compaction above a selected threshold. Thus, in some implementations, the course may be used by a tillage machine to selectively till portions of the surveyed field having soil compaction above a selected threshold. By identifying those areas of the surveyed worksite that have a soil compaction at or above a selected threshold, a user is able to follow the plotted course to selectively till selective areas of the field while avoiding disruption to other portions of the worksite. Further, the selective tilling saves time, reduces fuel consumption, and reduces wear and tear on the tillage machine.

In other implementations, the soil compaction map may be utilized to define a material transport course through the field. The material transport course may define a route through a field that is predicted to reduce effects of compaction on crops. In some implementations, the defined material transport course may have a distance that is larger than a shortest point-to-point course because, for example, the course may avoid one or more areas that are susceptible to compaction damage. In identifying a course, the costs associated with an increased transport distance, such as fuel and labor costs, may be weighed against the cost of future yield loss from increased compaction. In some implementations, other factors may be used to determine a route for a material transport course. Without limitation, these factors may include various forms of equipment wear, equipment consumables, and soil compaction remediation. Thus, in some instances, while a material transport course may have a distance that is greater than a shortest point-to-point distance, the cost associated with increased fuel and labor costs may be outweighed, for example, by increased crop yield. Thus, in some implementations, the material transport course may reduce a total length of the course while avoiding areas of increased compaction or areas susceptible to compaction. Consequently, a material transport course may reduce consumption of resources by reducing a total path traveled while also avoiding areas having increased soil compaction or otherwise reducing an amount of soil compaction resulting from the transport vehicles.

In still other implementations, crop yield analytics may be generated using the thermal latency information. Crop yield analytical information is obtained using crop stress information, and the crop stress information is derived from the thermal latency information obtained by UAVs, satellite, or other sensors (e.g., terrestrial-based sensors). In addition to the thermal latency information, other types of information may be incorporated to obtain the crop yield analytics. For example, manual crop scouting data, harvest crop yield data, crop model data, and other types of data may be utilized to determine the crop yield analytical information. The crop yield analytical information may be arranged in the form of a crop yield map. Among other information, the crop yield map identifies areas of a surveyed worksite that may result in reduced crop yield.

One or more action plans may be generated using the crop yield map. For example, action plans for selective tillage, crop irrigation, or drainage remediation or repair may be generated based on the crop yield map.

Still further, soil compaction information derived from the thermal latency information may be compared to soil compaction sample test data obtained from actual locations within the surveyed worksite (referred to as "ground-truth data"). The ground-truth data may be used to calibrate the soil compaction data derived from the thermal latency information to provide a more accurate representation of soil compaction within the surveyed worksite. A calibrated soil compaction map may be generated from this calibrated soil compaction data, and, as explained above, a selective tillage course or a material transport course, for example, may be generated based on the calibrated soil compaction map.

At 314, one or more aspects of an agricultural vehicle is controlled along the plotted course and according to the plan of action (e.g., the one or more areas of a worksite for which selective tillage is desired. The aspects of the agriculture vehicle include operation of or one or more components of the agricultural vehicle. For example, an agricultural vehicle that includes a tillage machine may be controlled according to a plan of action and a generated course along the worksite. One or more controllable aspects of the agricultural machine may include controllable subsystems and propulsion systems. The tillage machine is controlled along a generated course, such as by a controller (which may be similar to controller 214 described above), to selectively till one or more portions of a field having soil compaction at or above a selected threshold. Control of the tillage machine may include controlling when to engage tillage components with the ground, how deep the tillage components penetrate the soil, or a load applied by the tillage components to the ground; controlling a tire pressure; controlling a direction of the tillage machine; controlling a speed of the tillage machine; or controlling a combination of any of these or other aspects of the agricultural vehicle.

In other implementations, the agricultural vehicle may be a material transport vehicle, such as a tractor with a baler attachment, a trailer, or some other material transport device. As explained above, one or more aspects of such an agricultural vehicle may be controlled as the agricultural vehicle is moved along the plotted course. These aspects include, but are not limited to, altering a tire pressure, altering a direction of travel, and altering a speed of travel. Other aspects may also be controlled.

In some implementations, adjustment of different aspects of an agricultural machine may be performed simultaneously, sequentially, or both. For example, as a tillage machine moves across a field, a controller is operable to generate a signal to extend a till to contact the ground while simultaneously controlling a speed of the agricultural machine or a direction of the agricultural vehicle or both. Additionally, the controller may vary a load applied to the till to vary an amount by which the till penetrates the soil. Other aspects of the agricultural machine, e.g., other controllable subsystems, may be controlled as well.

Adjustments of aspects of an agricultural machine, such as controllable subsystems, may be pre-computed or computed dynamically in real time. Computing adjustments for different aspects of the agricultural machine may also occur periodically as the agricultural machine travels along the determined course. For example, as the agricultural machine approaches an area of increased soil compaction, a depth of penetration of the till may be increased. Again, the adjustments may be made based on the generated course, soil compaction map, and plan of action.

In some implementations, adjusting an aspect of an agricultural machine may include incorporating sensor data from one or more sensors that is sensing as the agricultural vehicle moves through a worksite along the determined course. Incorporating sensor data may include, for example, communication with one of sensors that is attached to agricultural vehicle (which may be similar to sensors 220 described above). Example sensors may include a geopositional sensor to control a speed or direction or both of the agricultural machine, a soil compaction sensor to sense a soil compaction level. Example sensors may also include one or more remote sensors (such as a remote contact soil temperature sensor, a non-contact soil temperature sensor, a soil moisture sensor, a soil type sensor, a soil organic matter sensor, or any other sensor operable to sense an aspect of the soil at the worksite). A controller of the agricultural machine may receive data from the sensors, whether remote or onboard of the agricultural machine, and incorporate the received data to alter an operational aspect of the agricultural machine.

While adjustability of aspects of the agricultural machine has been discussed, it is to be understood that the particular values for the adjustments are obtainable using a variety of technologies. These technologies include, for example, applying the obtained soil parameters to known equations, the use of lookup tables, fuzzy logic, neural networks, machine learning, rules-based systems, etc. Further, the adjustments applied to a sensed condition may be determined empirically, or otherwise. For example, adjustments may depend on soil type, moisture level, machine capabilities, etc.

Soil models may be used to estimate a soil moisture saturation percentage, and the estimated soil moisture saturation percentage may be used to improve a porosity determination. As mentioned above, machine learning is one technique that may be used to improve soil porosity estimates for a worksite over time. Improved soil porosity estimates, in turn, may be used to provide improved soil compaction data. A confidence level of soil moisture saturation or dehydration levels over the course of different measurements, a confidence level in SOM percentages, and sensor resolution (e.g., spatial resolution, thermal resolution, etc.) may go into a confidence level for soil compaction estimations at a selected level of spatial resolution.

In some implementations, absolute soil porosity and soil compaction values may be calculated. In other implementations, relative soil porosity and soil compaction values may be calculated. In some instances, an accuracy of soil-type maps (i.e., maps having data identifying types of soil) may influence whether absolute or relative soil porosity and soil compaction values are used for a particular worksite. In some implementations, two or more thermal images may be obtained during cloudy day sky conditions or at night in order to reduce an impact of unequal heating due to sunlight variations on the surface that may result from soil color, topography, etc.

In some implementations, pixels forming a soil parameter map may be classified into different types so that pixels representing bare soil are exclusively used in determining soil porosity. In such instances, the resulting soil parameter maps may use interpolated data to fill in soil parameter values for pixel locations previously excluded due to surface cover.

Thermal latency may be derived from two or more thermal image data sets taken of a soil of a worksite. The two or more thermal image data sets may be acquired over a selected period of time, such as when soil temperature is changing in response to changing air temperature or solar heating. In other instances, the soil may be allowed to come to a thermal equilibrium without solar influence (such as at night or during a prolonged period of cloud cover). A single soil thermal data map may be generated after air temperature has changed. In some implementations, an initial soil temperature may be assumed to be an initial ambient air temperature.

Figure 6:
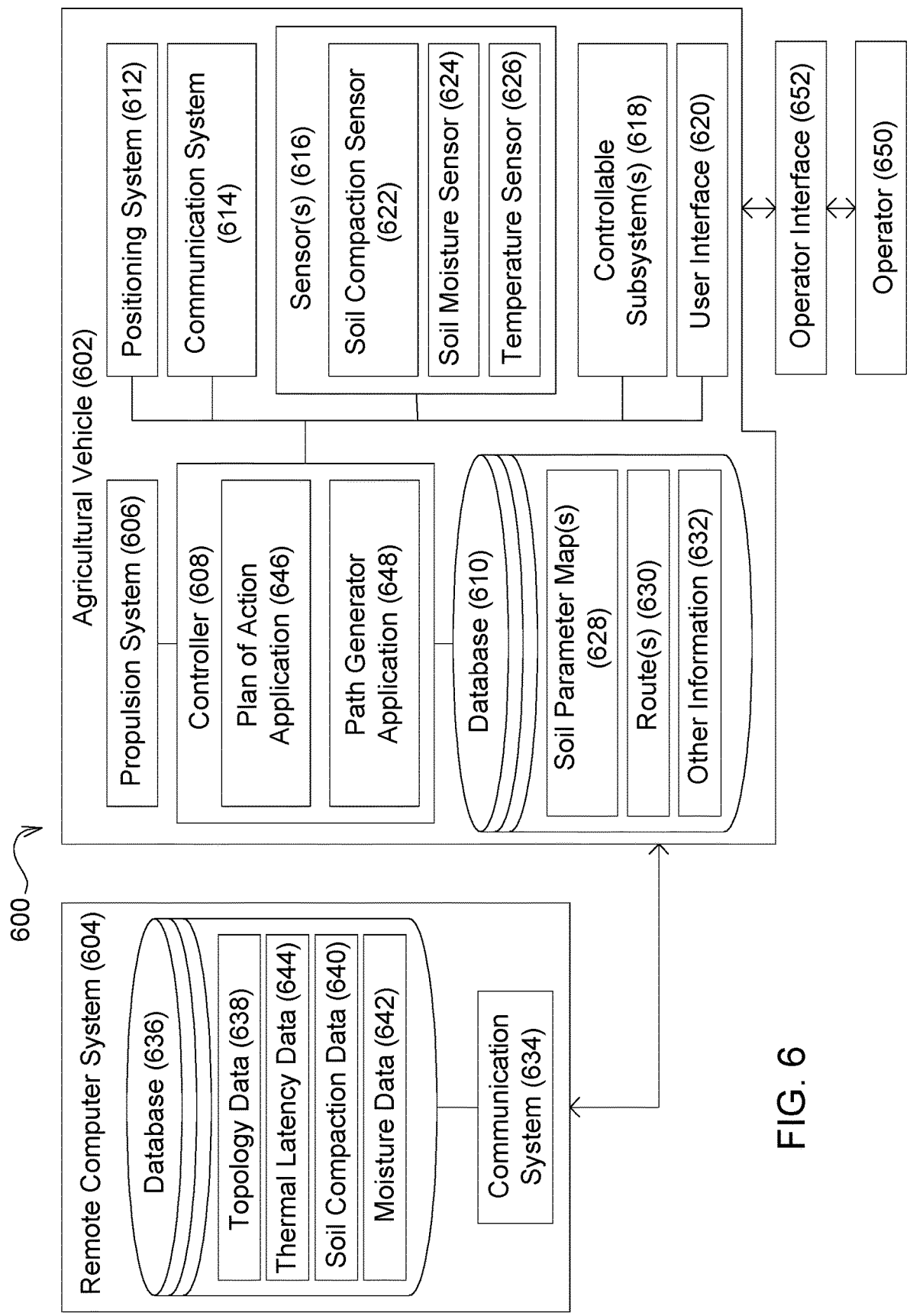
FIG. 6 is a block diagram of another example agricultural system, according to some implementations of the present disclosure.

FIG. 6 is a block diagram of an example agricultural system 600. The agricultural system 600 includes an agricultural vehicle 602 in communication with a remote computer system 604. The agricultural system 600 also includes an operator 650 and an operator interface 652. The operator interface 652 permits the operator 650 to interact, e.g., control, one or more aspects of or receive information regarding, the agricultural system 600, such as the agricultural vehicle 602. The remote computer system 604 may be a type of electronic computer operable to execute programs and store information electronically, as described in more detail below. The agricultural system 600 may be used for treating a worksite, such as by tilling one or more locations of the worksite. The agricultural system 600, in some implementation, may be similar to agricultural system 200, described above. The agricultural system 600 may be configured to assist a user, such as a farmer, to perform, for example, site-specific tillage of a worksite. The remote computer system 604 may be similar to remote computer system 206, described above. In other implementations, the agricultural system 600 may include additional components, such as a UAV, satellite, or other component.

Each of the agricultural vehicle 602 and the remote computer system 604 are shown as including various features. However, while FIG. 6 illustrates one example of how these features are distributed among the agricultural vehicle 602 and the remote computer system 604, the example of FIG. 6 is provided merely as an example. In other implementations, the various features may be distributed differently amongst the agricultural vehicle 602 and the remote computer system 604. Still further, in other implementations, the agricultural system 600 may include additional features, fewer features, or different features than those illustrated and described. Consequently, agricultural systems having other arrangements of features are contemplated within the scope of the present disclosure.

As shown, the agricultural vehicle 602 includes a propulsion system 606, a controller 608, a database 610, a positioning system 612, a communication system 614, one or more sensors 616, controllable susbsystems 618, and a user interface 620. As shown, the different components of the agricultural vehicle 602 are communicably connected. The propulsion system 606 is operable to move the agricultural vehicle 602 through a worksite, such as a field. The propulsion system 606 is coupled to and, in some implementations, controlled by, the controller 608. The controller 608 is also coupled to the positioning system 612. The positioning system 612 is operable to provide an indication of a location of the agricultural vehicle 602 within a worksite. The positioning system 612, in some implementations, may be a GPS or any other positioning system.

The controller 608 is coupled to the communication system 614 which enables communication between the agricultural vehicle 602 and the remote computer system 604. The controller 608 may be in the form of an electronic computer having one or more processors configured to execute applications and one or more memory devices configured to store data and programs electronically. Although a single remote computer system 604 is illustrated, in other implementations, the remote computer system 604 may be a plurality of remote computer systems. Further, in some implementations, the remote computer system 604 may be one or more remote servers. The controller 608 is also coupled to the one or more sensors 616, including, for example, a soil compaction sensor 622, a soil moisture sensor 624, a temperature sensor 626. The controller 608 is also coupled to the one or more controllable subsystems 618, such as controllable features on a tillage machine.

The controller 608 is coupled to database 610. The database 610 may be in the form of one or more electronic memory devices configured to store information electronically. The database 610 includes information such as a soil parameter map 628 (e.g., a soil compaction map, a soil moisture map, or a soil temperature map, a crop yield analytics map, or thermal latency map), an operation route 630, as well as other information 632, which may include information relevant to the operation of the agricultural vehicle 602. The soil parameter map 628 may include geo-referenced data for a worksite. The data may include data indicative of soil moisture, temperature, or compaction, or data derived from soil parameter data, such as estimated crop yield data, root restriction data, or other types of data, such as geopositional data. Also, while database 610 is illustrated as forming part of the agricultural vehicle 602, it is to be understood that database 610 may be deployed in another arrangement. For example, the database 610 may be partially located on the agricultural vehicle 602 and partially on the remote computer system 604, fully stored within the remote computer system 604, or fully or partially stored elsewhere, such as within a cloud-based infrastructure. Additionally, while the sensors 616 are shown specific to the agricultural vehicle 602, it is to be understood that at least some of the sensors 616 may be stationary sensors not configured to move with the agricultural vehicle 602, but to remain at a location within a worksite and accessed through communication system 614, in some implementations.

The remote computer system 604, in some implementations, includes a communication system 634 configured to allow for communication between the remote computer system 604 and the agricultural vehicle 602. The remote computer system 604 includes a database 636. The database 636 be one or more electronic memory devices and may store historic information, recently obtained data about a worksite, data related to the agricultural vehicle 602, or any combination of these types of data or other data. The database 636 may also contain other types of information, including data, applications, or both. For example, database 604 may include topology data 638 relative to a given worksite, soil compaction data 640, moisture data 642, and thermal latency data 644. Other types of data may also be included, such as geo-positional data, or other types of information, such as information related to the agricultural vehicle 602. Similar to the database 610, the database 636 may be partially located on the remote computer system 604, partially located on the agricultural vehicle 602 (such as part of the database 610), fully provided on the agricultural vehicle 602, or fully or partially stored elsewhere, such as within a cloud-based infrastructure.

In some implementations, at least a portion of the data stored within database 636 may be gathered by a remote sensor, for example a UAV (which may be similar to UAV 204 described above), a ground-based vehicle, or another source, such as radar or satellite imagery. In some implementations, remotely sensed data are compared to data collected from ground-based sensors, such as the sensors 616 coupled to the agricultural vehicle 602, or other sensors located throughout a worksite, in order to verify data from a remote site. Additionally, while data has been discussed as being obtainable from a UAV, in other instances, at least some of the data within database 636 may be collected from a sensor mounted on the ground, a terrestrial vehicle, a manned aircraft, a balloon, satellite, or any other mounting location.

Based on information obtained from the remote computer system 604, the database 610, or other external source, the controller 608 is operable to create a plan of action using a plan of action application 646. In the illustrated example, the controller 608 also includes a path generator application 648 operable to generate a course for the agricultural vehicle 602 across a worksite or a portion thereof. The plan of action application 646 and the path generator application 648 include software instructions that, when executed by the controller 608, causes the controller to generate a cause of action and a path across a worksite, respectively. The plan of action application 646, in some implementations, may generate a tillage plan using a compaction map generated for a given worksite. In the illustrated example, the agricultural vehicle 602 may be any agricultural vehicle operable to perform a tillage function. In some implementations, the agricultural vehicle 602 is operable to selectively till areas of a worksite based on a selected level of soil compaction as the agricultural vehicle 602 moves over the worksite. The controller 608 also includes the path generator application 648 that is operable to determine a path through a worksite based on or more inputs, such as soil parameter data, start and end data, waypoint data, or other data. Applicable path generators are described in more detail below.

Figure 7:
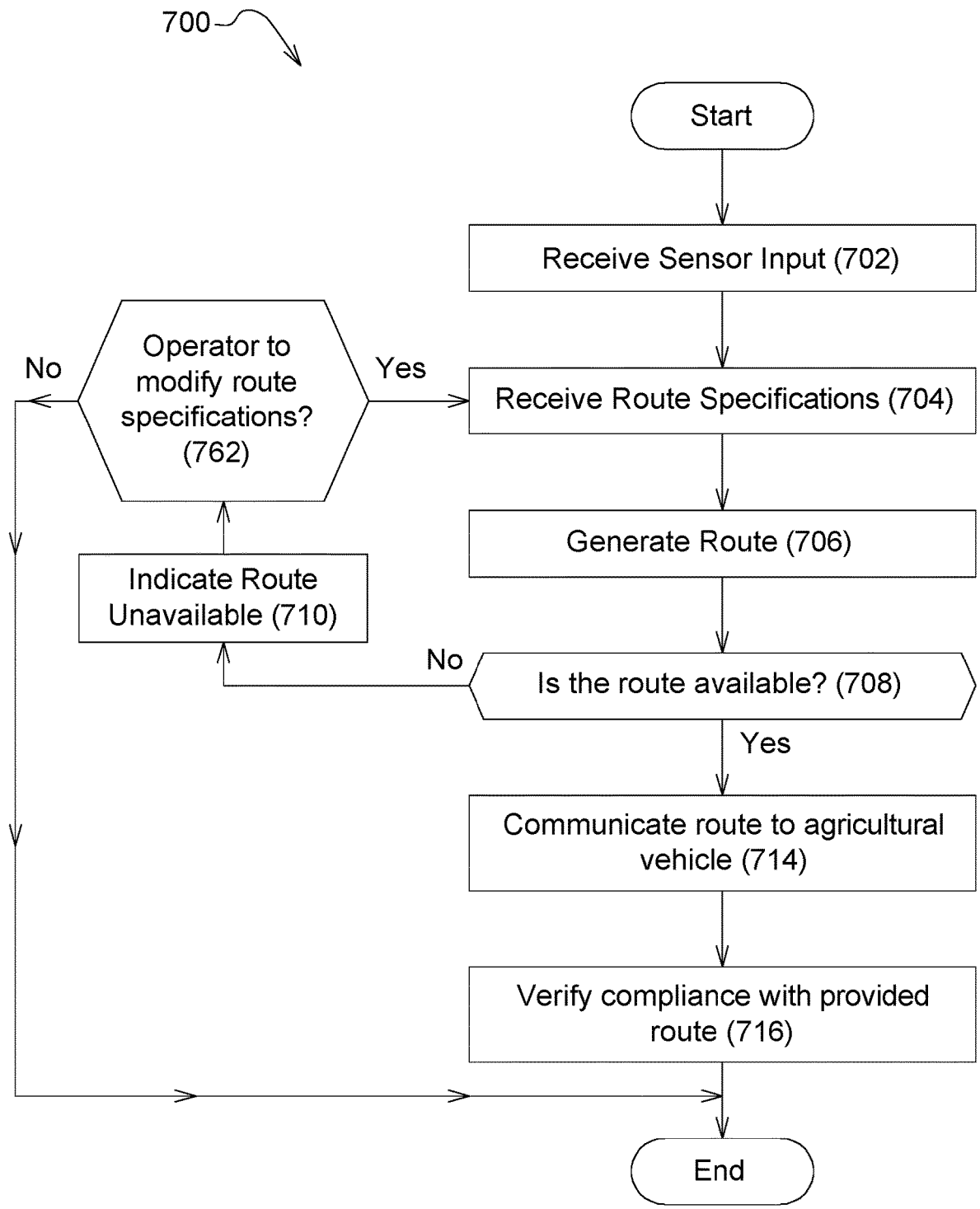
FIG. 7 is a flowchart of an example method for selectively tilling a worksite or a portion thereof, according to some implementations of the present disclosure.

FIG. 7 is a flowchart of an example method 700 for selectively tilling a worksite or portion thereof. The method 700 involves the use of soil compaction data having a spatial resolution, for example, in the centimeter range. The method 700 includes generation of a trafficability route through a worksite for an agricultural vehicle, such as agricultural vehicle 202 and 602. The trafficable route is determined by a route generator. In some implementations, the trafficability route is precomputed and loaded into an agricultural system, such as agricultural system 200 and 600. In some implementations, the trafficability route is generated by the agricultural system.

Different systems and methods have been described herein for determining input parameters for one or more aspects of an agricultural vehicle (e.g., propulsion systems and controllable subsystems) based on soil parameters. In some implementations, the soil parameters are used to identify a route for traversing a given worksite. For example, soil compaction information may be used both to identify areas for which tilling in desired (e.g., areas having a soil compaction at or above a selected level) and to define a route to and between those areas. For example, areas of a worksite having soil compaction that is below the threshold for tilling may nevertheless be of a level that traversal by the agricultural vehicle may result in the soil compaction that meets or exceeds the tillage threshold. Thus, the route across the worksite may selected to avoid areas that may result in soil compaction at or above the threshold for tillage after traversal by the agricultural vehicle. In other implementations, a distance of the route or a portion of the distance of the route may also be considered when determining the course of the route. Further, a distance of the route or distance of a portion of the route may be used to define the course of the route notwithstanding the fact that the resulting route passes over one or more areas that may produce a soil compaction that meets or exceeds the threshold value. In such instances, the agricultural vehicle may be used to till the areas that have a resulting soil compaction that exceeds the threshold after passage by the agricultural vehicle. Therefore, the distance of the course may be reduced while areas of the worksite for which tillage is applied may be increased above what is otherwise indicated by the original soil compaction data.

In other implementations, other soil parameter data may be used to determine aspects of the trafficable route. For example, soil moisture data may be used to determine whether a route is available at all due to the soil having a moisture level that would preclude travel by the agricultural vehicle. If the soil contains too much moisture, travel over the worksite along a route by a vehicle (such as an agricultural vehicle, a forestry vehicle, or a construction vehicle) may not be possible. The method 700 represents one example for generating a trafficable route and indicating whether the generated route is traversable by the vehicle. The generated route may be used by an agricultural vehicle to perform selective tilling or any other operation. For example, the generated route may be used by other vehicles, such as transport vehicles, to conduct operations or just to move across a worksite.

At 702, sensor input is received. The sensor input may include historic information, current information, or both about any of a wide variety of soil parameters that may influence route determination. Therefore, the received sensor input may include thermal latency, soil porosity, soil compaction, soil moisture, or soil temperature of a worksite. Further, the received sensor data may also include a plan of action, such as a plan of action determined by a plan of action application (e.g., plan of action applications 228 and 646). As explained above, a plan of action may be generated using sensor data or processed sensor data that is analyzed to determine areas of a worksite meeting a criterion. For example, sensor data may be derived soil parameter data, and one or more instances of the soil parameter data may meet or exceed a threshold that indicates those areas of the worksite in need of a treatment, such as tillage. A plan of action may be received as a route specification at 704.

At 704, route specifications are received. In some implementations, receiving route specifications includes receiving, through a user input, information about an operator's desired route. Route specifications may include at least one of a start point, an end point, one or more way points along the route between the start point and the end point, and a treatment plan according to a plan of action.

Additional or different route specifications are also contemplated. For example, an operator may desire to till one or more portions of a worksite based, for example, on a soil compaction value. In such instances, at 704, receiving route specifications may include an indication that an operator will be traversing an entirety of a worksite or a specified portion of a worksite. In another implementation, receiving route specifications may include receiving an indication from an operator of a desire to move an agricultural vehicle from a start point to an end point, with one or more waypoints in between. Route specification may include a wide variety of other specification as well, such as machine specifications for the agricultural vehicle (e.g., weight, tire pressure, tire or track configurations, etc.), or other information.

At 706, a route is generated based on the received sensor input and received route specifications. The route may be generated by a path generator application, which may be similar to the path generator application 648 described above. In some implementations, generating a route includes determining whether a route is even available for the agricultural vehicle, given the received route specifications and based on known information about the worksite. At 708, a determination is made as to whether a route is possible based on the received route specification, received senor input, and, optionally, other information. For example, areas in the worksite may exists that have a soil moisture content at a level that precludes an agricultural vehicle from traveling a route that meets all of the route specifications. Further, one or more areas of the worksite along the worksite may include slopes that pose a danger to the operator or agricultural vehicle or that are not possible to traverse in the agricultural vehicle.

In one example, a route generator application configured to generate a route may take into account information about the agricultural vehicle being used to traverse the route, such as weight of the agricultural vehicle, tire width, tire pressure, attached implements, etc. This information may affect whether the agricultural vehicle is able to traverse any given portion of the worksite in view of the agricultural vehicle information and worksite properties, e.g., the worksite topography, moisture content, soil temperature, etc. Whether an agricultural vehicle is able to traverse a worksite or portion thereof may involve, for example, a likelihood of the agricultural vehicle becoming immobilized within the worksite (e.g., due to excessive soil moisture) or whether travel of the agricultural vehicle may result in damage to the worksite beyond a desirable level (e.g., where moisture levels would permit travel of the agricultural vehicle, but such movement would cause damage to the soil (e.g., in the form of ruts) or damage to crops, for example).

At 710, if a route satisfying all of the conditions and route specifications is determined not to be possible, an indication is provided to an operator that the desired route is unavailable. For example, a route that satisfies the start point, the end point, and the waypoints may not be possible where the worksite includes areas that have excessive soil moisture levels that would preclude supporting the agricultural vehicle or a towed implement.

The indication that the route is unavailable may take many forms and may include a variety of different types of information. For instance, an operator may receive an indication identifying areas of the worksite over which travel is not possible. In other instances, the indication may identify areas of the worksite where a desired operation, such as tillage, is not possible. The indication to the operator may also include one or more reasons underlying the determination, and, in some implementations, the indication may also include one or more suggested alternate routes that conforms to a specified number of the specifications. The one or more suggested alternative routes may identify deviations that do not conform to the received specifications. Other types of indications may also be provided.

If one or more alternative routes is determined to be available, at 712, the operator is prompted to select the acceptable alternative route. In some implementations, an operator may be prompted to remove one or more waypoints, select a different start point, or a different end point, alter a size of the worksite to be treated, select a different agricultural operation (e.g., tillage or material transport), or otherwise modify the route specifications. The method 700 returns to 704 to receive these modifications to the route specifications. Alternatively, if one or more alternative routes is not available, method 700 ends. In other implementations, if one or more alternative routes is not available, the method may return to 704 to permit the operator to enter a new set of route specifications in an attempt to generate a satisfactory path through the worksite.

If a route satisfying the received route specifications is generated, then the generated route is communicated to the agricultural vehicle at 714. As noted above, treatment information may be included as part of the received route specification. Thus, the generated route may include treatment locations determined based on, for example, soil parameter data satisfying one or more criteria. In some implementations, the generated route is communicated to a controller of the agricultural vehicle. The controller may utilize the generated path and input from a positioning system, such as a GPS system, to position the agricultural vehicle at a desired start point and guide navigation of agricultural vehicle along the generated route.

In some implementations, the generated route is generated at a remote computer system source, such as remote computer system 206 and 604, and transmitted to the operator, for example, via a mobile computing device such as a mobile phone, tablet computer, or other computing device. In some implementations, the controller of the agricultural vehicle or another computing device operatively connected to the agricultural vehicle is operable to generate the route.

In some implementations, the generated route may be provided to the operator who then executes the route, in whole or in part, by manipulation of the controls of the agricultural vehicle. For example, in some instance, the operator may be responsible for controlling one or more of a direction of, a speed of, or a treatment to be performed by the agricultural vehicle while the controller is operable to control the remaining of the direction, speed, or treatment. In other instances, the operator operates the agricultural vehicle entirely according to the generated path. In still other instances, the controller may operate agricultural vehicle autonomously according to the determined route, including application of treatments at one or more locations satisfying treatment criteria. The generated route may be presented to an operator on an interface, such as interface 652, within or communicably coupled to the agricultural vehicle. In some implementations, the interface may be a display device or other device operable to present the generated route information to the operator. In some implementations, the generated route includes a set of instructions for the operator. In other implementations, the generated route is combined with information provided by a positioning system, such as positioning system 225 or 612, to provide directions for the operator on a display. In still other implementations, the controller of the agricultural vehicle utilizes the generated route and positional data to automatically control steering, drive functions of a propulsion system to navigate the agricultural vehicle. In some instances, the controller is also operable to control subsystems of the agricultural vehicle, such as to cause the agricultural vehicle to treat predetermined areas of the worksite.

At 716, compliance with the generated route is monitored. In some implementations, the controller of the agricultural vehicle indicates when a deviation is detected, for example on a display within agricultural vehicle. In other implementations, monitoring compliance with the generated route includes receiving geopositional information from a positioning system, comparing a measured position of the agricultural vehicle obtained from the positioning system to the generated route, and providing an indication of a deviation and remedial action. In some instances, the compliance monitoring may be performed by a system of the agricultural vehicle, such as the controller, by one or more remote computer system, such as remote computer system 206 and 604, or collaboratively between the controller and one or more remote computer systems. Thus, in some implementations, monitoring compliance includes the controller automatically receiving a position of agricultural vehicle from a positioning system, comparing the received position to the generated route, and automatically adjusting operation (e.g., speed, direction, treatment application, or a combination of these) to correct for a detected deviation. For example, in some implementations, the controller is operable to adjust a propulsion or steering system.

Figure 8:
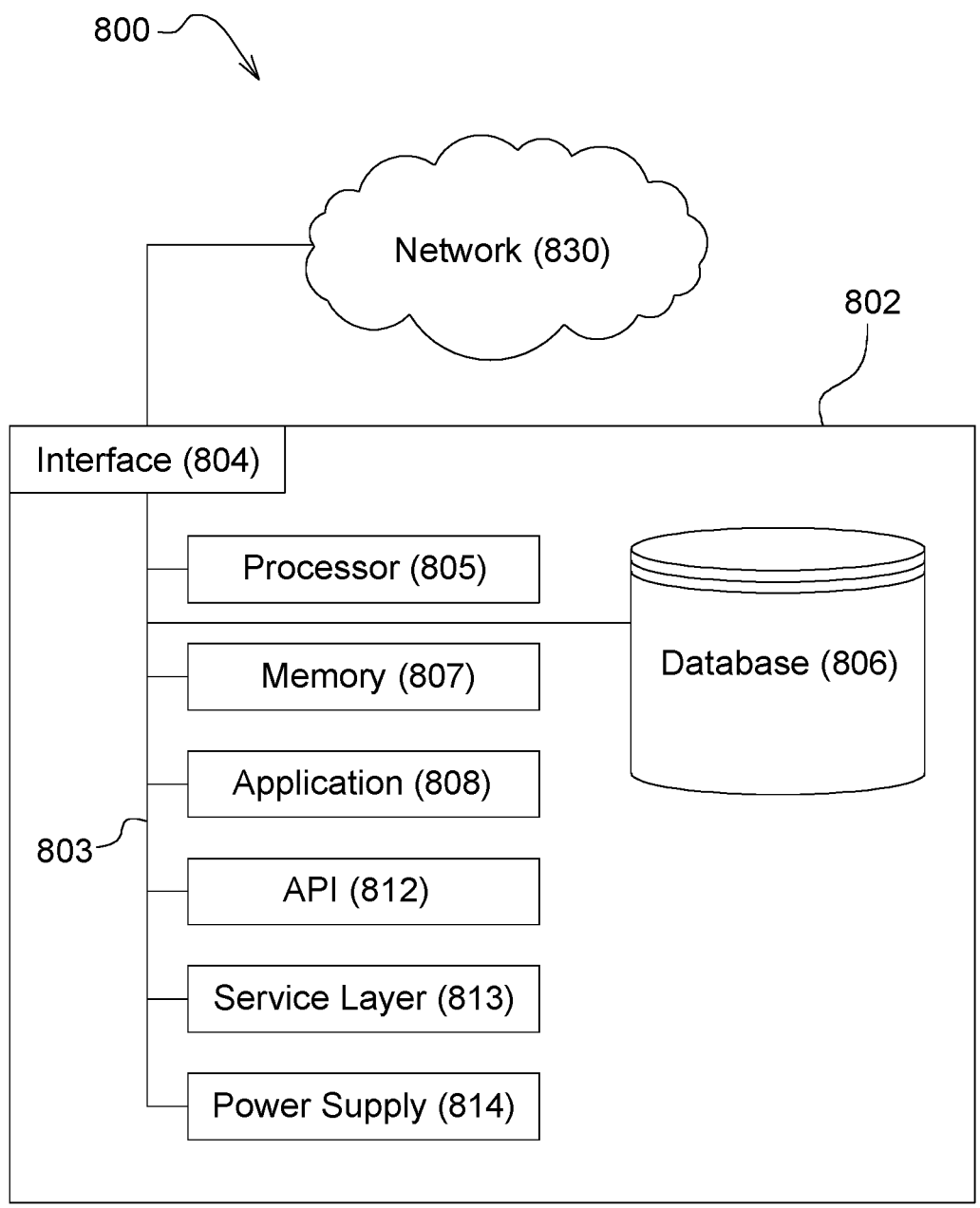
FIG. 8 is a block diagram illustrating an example computer system used to provide computational functionalities associated with described algorithms, methods, functions, processes, flows, and procedures as described in the present disclosure, according to some implementations of the present disclosure.

FIG. 8 is a block diagram of an example computer system 800 used to provide computational functionalities associated with described algorithms, methods, functions, processes, flows, and procedures described in the present disclosure, according to some implementations of the present disclosure. The illustrated computer 802 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 802 can include input devices such as keypads, keyboards, and touch screens that can accept user information. Also, the computer 802 can include output devices that can convey information associated with the operation of the computer 802. The information can include digital data, visual data, audio information, or a combination of information. The information can be presented in a graphical user interface (UI) (or GUI).

The computer 802 can serve in a role as a client, a network component, a server, a database, a persistency, or components of a computer system for performing the subject matter described in the present disclosure. The illustrated computer 802 is communicably coupled with a network 830. In some implementations, one or more components of the computer 802 can be configured to operate within different environments, including cloud-computing-based environments, local environments, global environments, and combinations of environments.

At a high level, the computer 802 is an electronic computing device operable to receive, transmit, process, store, and manage data and information associated with the described subject matter. According to some implementations, the computer 802 can also include, or be communicably coupled with, an application server, an email server, a web server, a caching server, a streaming data server, or a combination of servers.

The computer 802 can receive requests over network 830 from a client application (for example, executing on another computer 802). The computer 802 can respond to the received requests by processing the received requests using software applications. Requests can also be sent to the computer 802 from internal users (for example, from a command console), external (or third) parties, automated applications, entities, individuals, systems, and computers.

Each of the components of the computer 802 can communicate using a system bus 803. In some implementations, any or all of the components of the computer 802, including hardware or software components, can interface with each other or the interface 804 (or a combination of both), over the system bus 803. Interfaces can use an application programming interface (API) 812, a service layer 813, or a combination of the API 812 and service layer 813. The API 812 can include specifications for routines, data structures, and object classes. The API 812 can be either computer-language independent or dependent. The API 812 can refer to a complete interface, a single function, or a set of APIs.

The service layer 813 can provide software services to the computer 802 and other components (whether illustrated or not) that are communicably coupled to the computer 802. The functionality of the computer 802 can be accessible for all service consumers using this service layer. Software services, such as those provided by the service layer 813, can provide reusable, defined functionalities through a defined interface. For example, the interface can be software written in JAVA, C++, or a language providing data in extensible markup language (XML) format. While illustrated as an integrated component of the computer 802, in alternative implementations, the API 812 or the service layer 813 can be stand-alone components in relation to other components of the computer 802 and other components communicably coupled to the computer 802. Moreover, any or all parts of the API 812 or the service layer 813 can be implemented as child or sub-modules of another software module, enterprise application, or hardware module without departing from the scope of the present disclosure.

The computer 802 includes an interface 804. Although illustrated as a single interface 804 in FIG. 8, two or more interfaces 804 can be used according to particular needs, desires, or particular implementations of the computer 802 and the described functionality. The interface 804 can be used by the computer 802 for communicating with other systems that are connected to the network 830 (whether illustrated or not) in a distributed environment. Generally, the interface 804 can include, or be implemented using, logic encoded in software or hardware (or a combination of software and hardware) operable to communicate with the network 830. More specifically, the interface 804 can include software supporting one or more communication protocols associated with communications. As such, the network 830 or the interface's hardware can be operable to communicate physical signals within and outside of the illustrated computer 802.

The computer 802 includes a processor 805. Although illustrated as a single processor 805 in FIG. 8, two or more processors 805 can be used according to particular needs, desires, or particular implementations of the computer 802 and the described functionality. Generally, the processor 805 can execute instructions and can manipulate data to perform the operations of the computer 802, including operations using algorithms, methods, functions, processes, flows, and procedures as described in the present disclosure.

The computer 802 also includes a database 806 that can hold data for the computer 802 and other components connected to the network 830 (whether illustrated or not). For example, database 806 can be an in-memory, conventional, or a database storing data consistent with the present disclosure. In some implementations, database 806 can be a combination of two or more different database types (for example, hybrid in-memory and conventional databases) according to particular needs, desires, or particular implementations of the computer 802 and the described functionality. Although illustrated as a single database 806 in FIG. 8, two or more databases (of the same, different, or combination of types) can be used according to particular needs, desires, or particular implementations of the computer 802 and the described functionality. While database 806 is illustrated as an internal component of the computer 802, in alternative implementations, database 806 can be external to the computer 802.

The computer 802 also includes a memory 807 that can hold data for the computer 802 or a combination of components connected to the network 830 (whether illustrated or not). Memory 807 can store any data consistent with the present disclosure. In some implementations, memory 807 can be a combination of two or more different types of memory (for example, a combination of semiconductor and magnetic storage) according to particular needs, desires, or particular implementations of the computer 802 and the described functionality. Although illustrated as a single memory 807 in FIG. 8, two or more memories 807 (of the same, different, or combination of types) can be used according to particular needs, desires, or particular implementations of the computer 802 and the described functionality. While memory 807 is illustrated as an internal component of the computer 802, in alternative implementations, memory 807 can be external to the computer 802.

The application 808 can be an algorithmic software engine providing functionality according to particular needs, desires, or particular implementations of the computer 802 and the described functionality. For example, application 808 can serve as one or more components, modules, or applications. Further, although illustrated as a single application 808, the application 808 can be implemented as multiple applications 808 on the computer 802. In addition, although illustrated as internal to the computer 802, in alternative implementations, the application 808 can be external to the computer 802.

The computer 802 can also include a power supply 814. The power supply 814 can include a rechargeable or non-rechargeable battery that can be configured to be either user- or non-user-replaceable. In some implementations, the power supply 814 can include power-conversion and management circuits, including recharging, standby, and power management functionalities. In some implementations, the power-supply 814 can include a power plug to allow the computer 802 to be plugged into a wall socket or a power source to, for example, power the computer 802 or recharge a rechargeable battery.

There can be any number of computers 802 associated with, or external to, a computer system containing computer 802, with each computer 802 communicating over network 830. Further, the terms "client," "user," and other appropriate terminology can be used interchangeably, as appropriate, without departing from the scope of the present disclosure.

Moreover, the present disclosure contemplates that many users can use one computer 802 and one user can use multiple computers 802.

Described implementations of the subject matter can include one or more features, alone or in combination.

For example, in a first implementation, a computer-implemented method for selectively determining one or more areas of a worksite for treatment includes: receiving soil parameter data of a worksite; generating a soil parameter map based on the received soil parameter data; generating a plan of action based on the soil parameter map, the plan of action defining an operation of an agricultural machine according to the soil parameter map; and controlling the operation of the agricultural machine according to the plan of action.

The foregoing and other described implementations can each, optionally, include one or more of the following features:

A first feature, combinable with any of the following features, the method further including: receiving image data of the worksite; and extracting the soil parameter data of the worksite data from the received image data.

A second feature, combinable with any of the previous or following features, wherein the image data of the worksite includes thermal latency data, and wherein extracting the soil parameter data of the worksite from the received image data includes extracting soil compaction data of the worksite.

A third feature, combinable with any of the previous or following features, the method further including: detecting a soil measuring event and receiving the image data of the worksite upon detecting the soil measuring event.

A fourth feature, combinable with any of the previous or following features, wherein detecting a soil measuring event includes detecting one of a fully saturated soil moisture level or a fully dry soil moisture level.

A fifth feature, combinable with any of the previous or following features, wherein the soil parameter data include soil compaction data, wherein generating a soil parameter map based on the determined soil parameter data includes generating a soil compaction map, and wherein generating a plan of action based on the soil parameter map includes determining one or more locations of the worksite having soil compaction at or above a selected level, and wherein controlling the operation of the agricultural machine according to the plan of action includes operating the agricultural machine to selectively till the one or more locations of the worksite having soil compaction at or above the selected level.

A sixth feature, combinable with any of the previous features, the method further including: generating a course through the worksite based on the soil parameter map; and controlling at least one of direction and speed of the agricultural machine to cause the agricultural machine to follow the generated course.

In a second implementation, a non-transitory, computer-readable medium storing one or more instructions executable by a computer system to perform operations including: receiving soil parameter data of a worksite; generating a soil parameter map based on the received soil parameter data; generating a plan of action based on the soil parameter map, the plan of action defining an operation of an agricultural machine according to the soil parameter map; and controlling the operation of an agricultural machine according to the plan of action.

The foregoing and other described implementations can each, optionally, include one or more of the following features:

A first feature, combinable with any of the following features, the computer-readable medium further including computer readable instructions for causing one or more processors to perform operations including: receiving image data of the worksite; and extracting the soil parameter data of the worksite from the received image data.

A second feature, combinable with any of the previous or following features, wherein the image data of the worksite includes thermal latency data, and wherein extracting the soil parameter data of the worksite from the received image data includes extracting soil compaction data of the worksite.

A third feature, combinable with any of the previous or following features, the computer program product further includes computer readable instructions for causing the one or more processors to perform operations includes: detecting a soil measuring event; and receiving the image data of the worksite upon detecting the soil measuring event.

A fourth feature, combinable with any of the previous or following features, wherein detecting a soil measuring event includes detecting one of a fully saturated soil moisture level or a fully dry soil moisture level.

A fifth feature, combinable with any of the previous or following features, wherein the soil parameter data includes soil compaction data, wherein generating a soil parameter map based on the determined soil parameter data includes generating a soil compaction map, wherein generating a plan of action based on the soil parameter map includes determining one or more locations of the worksite having soil compaction at or above a selected level, and wherein controlling the operation of the agricultural machine according to the plan of action includes operating the agricultural machine to selectively till the one or more locations of the worksite having soil compaction at or above the selected level.

A sixth feature, combinable with any of the previous features, the method further including computer readable instructions for causing the one or more processors to perform operations including: generating a course through the worksite based on the soil parameter map; and controlling at least one of direction and speed of the agricultural machine to cause the agricultural machine to follow the generated course.

In a third implementation, a computer-implemented system, including one or more processors and a non-transitory computer-readable storage medium coupled to the one or more processors and storing programming instructions for execution by the one or more processors, the programming instructions instructing the one or more processors to: receive soil parameter data of a worksite; generate a soil parameter map based on the received soil parameter data; generate a plan of action based on the soil parameter map, the plan of action defining an operation of an agricultural machine according to the soil parameter map; and control the operation of the agricultural machine according to the plan of action.

The foregoing and other described implementations can each, optionally, include one or more of the following features:

A first feature, combinable with any of the following features, wherein the programming instructions include programming instructions operable to instruct the one or more processors to: receive image data of the worksite; and extract the soil parameter data of the worksite from the received image data.

A second feature, combinable with any of the previous or following features, wherein the image data of the worksite include thermal latency data, and wherein the programming instructions operable to instruct the one or more processors to extract the soil parameter data of the worksite from the received image data include programming instructions operable to instruct the one or more processors to extract soil compaction data of the worksite.

A third feature, combinable with any of the previous or following features, the computer-implemented system further including programming instructions to instruct the one or more processors to: detect a soil measuring event; and receive the image data of the worksite upon detecting the soil measuring event.

A fourth feature, combinable with any of the previous or following features, wherein the programming instructions operable to instruct the one or more processors to detect a soil measuring event include programming instructions operable to instruct the one or more processors to detect one of a fully saturated soil moisture level or a fully dry soil moisture level.

A fifth feature, combinable with any of the previous features, wherein the soil parameter data include soil compaction data, wherein the programming instructions operable to instruct the one or more processors to generate a soil parameter map based on the determined soil parameter data include programming instructions operable to instruct the one or more processors to generate a soil compaction map, wherein the programming instructions operable to instruct the one or more processors generating a plan of action based on the soil parameter map include programming instructions operable to instruct the one or more processors to determine one or more locations of the worksite having soil compaction at or above a selected level, and wherein the programming instructions operable to instruct the one or more processors to control the operation of the agricultural machine according to the plan of action include programming instructions operable to instruct the one or more processors to operate the agricultural machine to selectively till the one or more locations of the worksite having soil compaction at or above the selected level.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as standalone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/nonvolatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

The present disclosure provides methods and systems for selectively treating a worksite, such as a field or portion of a field, based on collected soil parameter data having granular spatial resolution, such as in the millimeter or centimeter range. The methods and systems reduce time and expense associated with treating an entirety of the worksite that would otherwise be used. Without in any way limiting the scope, interpretation, or application of the claims appearing below, a technical effect of one or more of the example embodiments disclosed herein is conservation of resources, including temporal resources, pecuniary resources, and equipment life resources.

While the above describes example implementation of the present disclosure, these descriptions should not be viewed in a limiting sense. Rather, other variations and modifications may be made without departing from the scope and spirit of the present disclosure as defined in the appended claims.

What is claimed is:

1. A computer-implemented method performed by one or more processors for selectively determining one or more areas of a worksite for treatment, the method comprising the following operations:
   receiving soil parameter data of a worksite;
   generating a soil parameter map based on the received soil parameter data;
   generating a plan of action based on the soil parameter map, the plan of action defining an operation of an agricultural machine according to the soil parameter map; and
   controlling the operation of the agricultural machine according to the plan of action,
   wherein the soil parameter data comprise soil compaction data.

2. The computer-implemented method of claim 1, further comprising:
   receiving image data of the worksite; and
   extracting the soil parameter data of the worksite from the received image data.

3. The computer-implemented method of claim 2, wherein the image data of the worksite comprises thermal latency data, and wherein extracting the soil parameter data of the worksite from the received image data comprises extracting the soil compaction data of the worksite.

4. The computer-implemented method of claim 1, further comprising:
   detecting a soil measuring event; and
   receiving image data of the worksite upon detecting the soil measuring event.

5. The computer-implemented method of claim 4, wherein detecting a soil measuring event comprises detecting one of a fully saturated soil moisture level or a fully dry soil moisture level.

6. The computer-implemented method of claim 1,
   wherein generating a soil parameter map based on the determined soil parameter data comprises generating a soil compaction map,
   wherein generating a plan of action based on the soil parameter map comprises determining one or more locations of the worksite having soil compaction at or above a selected level, and
   wherein controlling the operation of the agricultural machine according to the plan of action comprises operating the agricultural machine to selectively till the one or more locations of the worksite having soil compaction at or above the selected level.

7. The computer-implemented method of claim 1, further comprising:
   generating a course through the worksite based on the soil parameter map; and
   controlling at least one of direction and speed of the agricultural machine to cause the agricultural machine to follow the generated course.

8. A computer program product encoded on a non-transitory medium, the computer program product comprising computer readable instructions for causing one or more processors to perform operations comprising:
   receiving soil parameter data of a worksite;
   generating a soil parameter map based on the received soil parameter data;
   generating a plan of action based on the soil parameter map, the plan of action defining an operation of an agricultural machine according to the soil parameter map; and
   controlling the operation of an agricultural machine according to the plan of action,
   wherein the soil parameter data comprise soil compaction data.

9. The computer program product of claim 8, further comprising computer readable instructions for causing one or more processors to perform operations comprising:
   receiving image data of the worksite; and
   extracting the soil parameter data of the worksite from the received image data.

10. The computer program product of claim 9, wherein the image data of the worksite comprises thermal latency data, and wherein extracting the soil parameter data of the worksite from the received image comprises extracting the soil compaction data of the worksite.

11. The computer program product of claim 8, further comprising computer readable instructions for causing the one or more processors to perform operations comprising:
   detecting a soil measuring event; and
   receiving image data of the worksite upon detecting the soil measuring event.

12. The computer program product of claim 11, wherein detecting a soil measuring event comprises detecting one of a fully saturated soil moisture level or a fully dry soil moisture level.

13. The computer program product of claim 8,
   wherein generating a soil parameter map based on the determined soil parameter data comprises generating a soil compaction map,
   wherein generating a plan of action based on the soil parameter map comprises determining one or more locations of the worksite having soil compaction at or above a selected level, and
   wherein controlling the operation of the agricultural machine according to the plan of action comprises operating the agricultural machine to selectively till the one or more locations of the worksite having soil compaction at or above the selected level.

14. The computer program product of claim 8, further comprising computer readable instructions for causing the one or more processors to perform operations comprising:
   generating a course through the worksite based on the soil parameter map; and
   controlling at least one of direction and speed of the agricultural machine to cause the agricultural machine to follow the generated course.

15. An agricultural machine for selectively determining one or more areas of a worksite for treatment, the agricultural machine comprising:
   one or more processors; and
   a non-transitory computer-readable storage medium coupled to the one or more processors and storing programming instructions for execution by the one or more processors, the programming instructions instruct the one or more processors to:
   receive soil parameter data of a worksite;
   generate a soil parameter map based on the received soil parameter data;
   generate a plan of action based on the soil parameter map, the plan of action defining an operation of the agricultural machine according to the soil parameter map; and
   control the operation of the agricultural machine according to the plan of action, wherein the soil parameter data comprise soil compaction data.

16. The agricultural machine of claim 15, wherein the programming instructions comprise programming instructions operable to instruct the one or more processors to:
   receive image data of the worksite; and
   extract the soil parameter data of the worksite data from the received image data.

17. The agricultural machine of claim 16, wherein the image data of the worksite comprises thermal latency data, and wherein the programming instructions operable to instruct the one or more processors to extract the soil parameter data of the worksite from the received image data comprise programming instructions operable to instruct the one or more processors to extract the soil compaction data of the worksite.

18. The agricultural machine of claim 15, further comprising programming instructions to instruct the one or more processors to:
   detect a soil measuring event; and
   receive image data of the worksite upon detecting the soil measuring event.

19. The agricultural machine of claim 18, wherein the programming instructions operable to instruct the one or more processors to detect a soil measuring event comprise programming instructions operable to instruct the one or more processors to detect one of a fully saturated soil moisture level or a fully dry soil moisture level.

20. The agricultural machine of claim 15,
   wherein the programming instructions operable to instruct the one or more processors to generate a soil parameter map based on the determined soil parameter data comprise programming instructions operable to instruct the one or more processors to generate a soil compaction map,
   wherein the programming instructions operable to instruct the one or more processors generating a plan of action based on the soil parameter map comprise programming instructions operable to instruct the one or more processors to determine one or more locations of the worksite having soil compaction at or above a selected level, and
   wherein the programming instructions operable to instruct the one or more processors to control the operation of the agricultural machine according to the plan of action comprise programming instructions operable to instruct the one or more processors to operate the agricultural machine to selectively till the one or more locations of the worksite having soil compaction at or above the selected level.

* * * * *